United States Patent [19]
Gross et al.

[11] Patent Number: 6,093,792
[45] Date of Patent: Jul. 25, 2000

[54] BIORESORBABLE COPOLYMERS

[75] Inventors: Richard A. Gross, Plainview, N.Y.; Xianhai Chen, Lowell; Stephen P. McCarthy, Tyngsboro, both of Mass.

[73] Assignee: University of Massachusetts, Boston, Mass.

[21] Appl. No.: 09/154,332

[22] Filed: Sep. 16, 1998

Related U.S. Application Data

[60] Provisional application No. 60/059,013, Sep. 16, 1997.

[51] Int. Cl.$^7$ .................................................. C08G 63/08
[52] U.S. Cl. ........................... 528/354; 528/196; 528/198; 528/303
[58] Field of Search .................... 528/354, 303, 528/196, 198

[56] References Cited

U.S. PATENT DOCUMENTS

| | | | |
|---|---|---|---|
| 4,481,353 | 11/1984 | Nyilas et al. | 528/303 |
| 4,916,193 | 4/1990 | Tang et al. | 525/413 |
| 5,066,772 | 11/1991 | Tang et al. | 528/354 |
| 5,286,763 | 2/1994 | Gerhart et al. | 514/772.4 |
| 5,359,026 | 10/1994 | Gruber | 528/354 |
| 5,399,665 | 3/1995 | Berrera et al. | 528/354 |
| 5,502,158 | 3/1996 | Sinclair et al. | 528/354 |
| 5,594,095 | 1/1997 | Gruber et al. | 528/354 |
| 5,654,381 | 8/1997 | Hrkach et al. | 525/450 |
| 5,747,637 | 5/1998 | Shinoda et al. | 528/354 |

FOREIGN PATENT DOCUMENTS 0 334 062 A2   1/1989   European Pat. Off. .

OTHER PUBLICATIONS

Dirk W. Grijpma, Albert J. Pennings, "(Co)polymers of . . . Mechanical properties", Macromol. Chem. Phys. 195, 1649–1663 (1994).

Chiellini et al., "Novel Hydroxyl Containing . . . Cyclic Anhydrides", Journal of Bioactive and Compatible Compatible Polymers, vol. 9, 153–169, (Apr. 1994).

Acemoglu et al., "Novel Bioerodible . . . Pharmaceutical Applications", Macromolecules, 28, 3030–3037 (1995).

Ouchi et al., "Synthesis . . . Pendant Groups", Journal of Polymer Science, Part A: Polymer Chemistry, vol. 35, 377–383 (1997).

John et al., "Synthesis . . . Based Copolymers", Journal of Polymer Science, Part A: Polymer Chemistry, 35, 1901–1907 (1997).

Elisseeff et al., Synthesis and Characterization . . . Poly( . . . acid), Macromolecules, vol. 30, No. 7, Notes 2183 (1997).

Schmidt et al., "Copolymerization . . . L–Lactide", Macromolecules, vol. 29, 3674–3680 (1996).

Klee et al., "Development . . . L–Lactide", Biomaterial–Tissue Interfaces, Advances in Biomaterials, vol. 10, 431–437 (1992).

Grijpma et al., "Poly . . . cartonate", Polymer, vol. 34, No. 7, 1993.

Barrera et al., "Copolymerization . . . Poly(lactic acid–colysine)", Macromolecules, vol. 28, 425–432 (1995).

Cai Jie & K. J. Zhu, "Preparation . . . Poly", Polymer International, vol. 42, 373–379 (1997).

Dirk W. Grijpma and Albert J. Pennings, "(Co)polymers of . . . degradation", Macromol. Chem. Phys., vol. 195, 1633–1647 (1994).

*Primary Examiner*—Terressa M. Boykin
*Attorney, Agent, or Firm*—Fish & Richardson P.C.

[57] ABSTRACT

This invention relates to high molecular weight bioresorbable copolymers constructed to be useful for specific applications in the biomedical arts. Also provided is a new cyclic carbonate monomer, and copolymers containing the new monomers.

39 Claims, 2 Drawing Sheets

BIORESORBABLE COPOLYMERS

CROSS REFERENCE TO RELATED APPLICATIONS

This application claims priority from U.S. Provisional Application Ser. No. 60/059,013 filed on Sep. 16, 1997.

STATEMENT AS TO FEDERALLY SPONSORED RESEARCH

This invention was made with Government support under grant number 09-07525-1 awarded by the National Science Foundation Biodegradable Polymer Research Center (NSF-BPRC). The Government may have certain rights in the invention.

BACKGROUND OF THE INVENTION

This invention relates to high molecular weight bioresorbable copolymers constructed to be useful for specific applications in the biomedical arts. The invention also provides three new cyclic carbonate monomers, copolymers containing the new monomers, and various methods of making and using the monomers and copolymers.

Degradable polymers have been used as implantable biomaterials and drug delivery systems. Biodegradable material implants can be used to gradually transfer load to a healing area and need not be removed subsequent to their use. For example, [L]-Poly(lactic acid) ([L]-PLA), a bioresorbable polymer, has been used for many years and has proved to be sterilizable and of low toxicity. [L]-PLA-based materials have shown favorable biocompatibility and have gained wide acceptability for applications that require bioresorption in vivo.

The degradation rate of [L]-PLA based polymeric materials is a function of the amorphous/crystalline and hydrophilic/hydrophobic properties. Strategies to regulate these factors have involved copolymerizations of [L]-lactide with [D]-lactide, glycolide, ethylene oxide, ε-caprolactone, and monomers that, upon ring-opening, provide amino acid repeat units. Alternatively, workers have attempted to 'tailor' PLA physico-mechanical properties and hydrolytic degradability by blending PLA with other polymers.

For example, U.S. Pat. No. 5,066,772 to Tang et al. describes bioabsorbable copolymers containing carbonate repeating units and hydroxycarboxylic acid repeating ester units. Polyesters with pendant carboxyl functional groups such as poly(malic acid) have been described, for example in Ouchi et al., Makromol. Chem., 190:1523 (1990). Polyesters with pendant amino functional groups such as poly ([L]-serine ester) are also known (see, e.g., Fietier et al., Polym. Bull. (Berlin), 24:349 (1990)), as are polydepsipeptides (morpholine-2,5-dione derivatives) with pendant carboxyl, amino, or thiol groups (In't Veld et al., Makromol. Chem., 193:2713 (1992)). PLA-based amine functionalized copolymers have also been reported (Barrera et al., Macromolecules, 28:425 (1995); Barrera et al., J. Am. Chem. Soc., 115:11010 (1993)).

SUMMARY OF THE INVENTION

The invention is based on the discovery that new, high molecular weight, stable, bioresorbable functionalized copolymers can be produced by polymerizing specific comonomers, such as lactone, lactam, and cyclic carbonate comonomers, to provide bioresorbability, under particular reaction conditions. The new copolymers are highly functionalized by the inclusion of a variety of pendant groups, and as a result are highly adaptable and able to interact with many useful and biologically active substrates to form copolymer compositions.

For example, the bioresorbable copolymers with pendant hydroxy, amine, carboxylic acid, and other groups allow binding with various bioactive molecules to provide timed release of such molecules. In this way, drugs can be effectively introduced into specific areas of the body, e.g., in a surgical operation, resulting in long-term drug delivery under well-defined, time-controlled conditions. In addition, the pendant functional groups provide specific anchor points for interactions with cell types for tissue engineering applications and facilitation of growth of cells, e.g., endothelial cells, on surfaces.

The functionalized copolymers, and compositions including the coplymers, can be easily processed in many ways to produce films, foams, various molded articles, laminates, spun-bonded nonwoven materials such as filaments, adhesives, and coatings. Other applications are in the area of functionalization of foams and other surfaces.

In general, the invention features a bioresorbable copolymer composition including products of a reaction between: (a) a first comonomer including lactones, lactides, lactams, thiolactones, and nonfunctionalized cyclic carbonates; and (b) a second, functionalized, cyclic carbonate comonomer, wherein the second comonomer is functionalized by a substituent group including alkenes, protected hydroxyl groups and protected carboxyl groups; wherein the hydroxyl groups are protected by hydroxyl protecting groups including ketals, acetals, or benzyl ethers; and wherein the carboxyl groups are protected by carboxyl protecting groups including benzyl esters. This composition can have pharmaceutical value, when a pharmaceutically active substance is linked to the copolymer.

For example, the second, functionalized, cyclic carbonate comonomer can have the formula

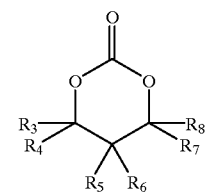

wherein $R_3$, $R_4$, $R_5$, $R_6$, $R_7$, and $R_8$ are substituent groups including hydrogen atoms, alkenes, protected hydroxyl groups, and protected carboxyl groups; wherein the hydroxyl groups are protected by hydroxyl protecting groups including ketals, acetals, and benzyl ethers; and wherein the carboxyl groups are protected with carboxyl protecting groups including benzyl esters; with the proviso that not all R groups can be hydrogen.

In this copolymer composition, any of $R_3$, $R_4$, $R_5$, $R_6$, $R_7$, and $R_8$ can form cyclic linkages with each other. Specific functionalized cyclic carbonate comonomers include 2,4-dioxaspiro[5.5]undec-8-ene-3-one (HTC), 1,2-O-isopropylidene-D-xylofuranose-3,5-cyclic carbonate (IPXTC), and 9,9-dimethyl-2,4,8,10-tetraoxaspiro[5.5] undecan-3-one (DTOUD). A homopolymer of the IPXTC monomer is can also be made.

The invention also features bioresorbable copolymer compositions of the formula

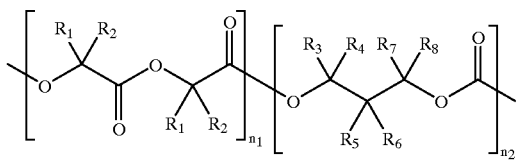

wherein $n_1$ and $n_2$ are 1 to 20,000; $R_1$ and $R_2$ are hydrogen, short chain or medium chain alkyl; and $R_3$, $R_4$, $R_5$, $R_6$, $R_7$, and $R_8$ are substituent groups including hydrogen atoms, alkenes, amines, carboxyl groups, thiols, epoxides, hydroxyl groups, esters, ethers, amides, thioethers, protected thiol groups, protected carboxyl groups, and protected hydroxyl groups, wherein the protected hydroxyl groups are protected by hydroxyl protection groups including ketals, acetals, and benzyl ethers; and wherein the protected carboxyl groups are protected with carboxyl protecting groups including benzyl esters; with the proviso that not all R are hydrogen.

Further, the invention features a bioresorbable copolymer composition of the formula

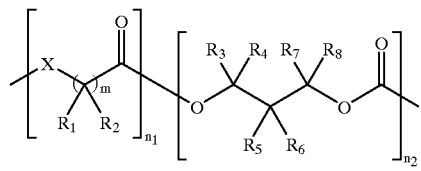

wherein m is 1 to 5; X is NH or S; $n_1$ and $n_2$ are 1 to 20,000; $R_1$ and $R_2$ are hydrogen, short chain or medium chain alkyl; and $R_3$, $R_4$, $R_5$, $R_6$, $R_7$, and $R_8$ are substituent groups including hydrogen atoms, alkenes, amines, carboxyl groups, thiols, epoxides, hydroxyl groups, esters, ethers, amides, thioethers, protected thiol groups, protected carboxyl groups, and protected hydroxyl groups, wherein the protected hydroxyl groups are protected by hydroxyl protection groups including ketals, acetals, and benzyl ethers; and wherein the protected carboxyl groups are protected with carboxyl protecting groups including benzyl esters; with the proviso that not all R are hydrogen.

The invention further features a bioresorbable copolymer composition of the formula

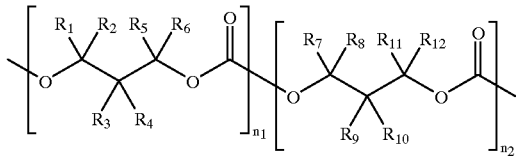

wherein $n_1$ and $n_2$ are 1 to 20,000; $R_1$, $R_2$, $R_3$, $R_4$, $R_5$, and $R_6$ are substituent groups including hydrogen atoms, alkanes, and ethers; and $R_7$, $R_8$, $R_9$, $R_{10}$, $R_{11}$, and $R_{12}$ are substituent groups including hydrogen atoms, alkenes, amines, carboxyl groups, thiols, epoxides, hydroxyl groups, esters, ethers, amides, thioethers, protected thiol groups, protected carboxyl groups, and protected hydroxyl groups, wherein the protected hydroxyl groups are protected by hydroxyl protection groups including ketals, acetals, and benzyl ethers; and wherein the protected carboxyl groups are protected with carboxyl protecting groups including benzyl esters; with the proviso that not all $R_7$, $R_8$, $R_9$, $R_{10}$, $R_{11}$ and $R_{12}$ are hydrogen.

In another aspect, the invention features a method of preparing a functionalized bioresorbable copolymer composition by: (a) obtaining a first comonomer including lactones, lactams, thiolactones, and nonfunctionalized cyclic carbonates; (b) obtaining a second, functionalized, cyclic carbonate comonomer, wherein the second comonomer is functionalized by a substituent group including alkenes, protected hydroxyl groups, and protected carboxyl groups; wherein the hydroxyl groups are protected by hydroxyl protection groups including ketals, acetals, and benzyl ethers; and wherein the carboxyl groups are protected by carboxyl protection groups including benzyl esters; and, (c) carrying out a copolymerization reaction between the first comonomer and the second, functionalized, cyclic carbonate comonomer under conditions which allow the formation of a functionalized bioresorbable copolymer composition.

In this method, the copolymerization can be catalysed with a catalyst selected from $Sn(Oct)_2$, $ZnEt_2\cdot H_2O$, $AlEt_3$, $Al(isobutyl)_3$, $Al(O\text{-secbutyl})_3$, $Al(O\text{-isopropyl})_3$, $Sn(C_6H_5)_4$, $La(OR)_3$, and $Y(OR)_3$, wherein R is ethyl, isobutyl, secbutyl, or isopropoxyl.

The method can further include the step of epoxidizing alkene groups of the functionalized bioresorbable copolymer subsequent to carrying out the copolymerization reaction, thereby creating epoxide groups, and can further include the step of converting the epoxide groups of the functionalized bioresorbable copolymer to hydroxyl groups subsequent to epoxidizing the alkene groups.

The method can also further include the step of removing the hydroxyl protecting groups of the functionalized bioresorbable polymer subsequent to carrying out the catalysed copolymerization reaction, thereby introducing hydroxyl groups. In addition, the method can further include the step of further functionalizing the hydroxyl groups, wherein the hydroxyl groups are functionalized by a substituent group including esters, ethers, amines, and carboxylic acids.

In yet another aspect, the invention features a pharmaceutically active bioresorbable copolymer composition including a copolymer of the invention and a pharmaceutically active substance, e.g., proteins, glycoproteins, anticancer drugs, and antihypertensive drugs, linked to the copolymer. The invention also includes a method of making a pharmaceutically active bioresorbable copolymer composition by: (a) producing a bioresorbable copolymer composition including the steps of: (i) obtaining a first comonomer including lactones, lactams, thiolactones, and nonfunctionalized cyclic carbonates; (ii) obtaining a second, functionalized, cyclic carbonate comonomer, wherein the second comonomer is functionalized by a substituent group including alkenes, protected carboxyl groups, and protected hydroxyl groups; wherein the hydroxyl groups are protected by hydroxyl protecting groups including ketals, acetals, and benzyl ethers; and wherein the carboxyl groups are protected by carboxyl protecting groups including benzyl esters; (iii) carrying out a catalysed copolymerization reaction between the first comonomer and the second, functionalized, cyclic carbonate comonomer under conditions which allow the formation of a functionalized bioresorbable copolymer composition; and (b) contacting the bioresorbable copolymer composition with a pharmaceutically active substance under conditions which allow bonding between the copolymer and the pharmaceutically active substance.

The method can further include the steps of crosslinking the bioresorbable copolymer with a crosslinking substance, and reacting the functionalized, bioresorbable copolymer composition with a second bioresorbable copolymer or a monomer including lactones, lactams, thiolactones, unfunctionalized cyclic carbonates, functionalized cyclic carbonates, and N-carboxy anhydrides, thereby forming a graft copolymer.

The invention also includes therapeutic articles of manufacture including the pharmaceutically active bioresorbable copolymer compositions.

A "bioresorbable" compound is one that can be degraded to a low molecular weight and may or may not be eliminated from a living organism. Such compounds may also be metabolized by organisms. A "biodegradable" compound is one that can be acted upon biochemically by living cells or organisms, or parts of these systems, or reagents commonly found in such cells, organisms, or systems, including water, and broken down into lower molecular weight products. The organism may play an active or passive role in such actions.

Chemical reactions can include the formation or dissociation of ionic, covalent, or noncovalent structures through known means. "Bonds," "bonding," or "linkages" are ionic, covalent, or noncovalent bonds of all types. Physical reactions can include changes in environmental conditions such as pH, ionic strength, and temperature. Short and medium chain alkyl groups are those containing 1 to 4 carbon atoms, and 5 to 12 carbon atoms, respectively.

A "polymer" can be a homopolymer and/or copolymer, or blends or physical mixtures thereof. Unless the optical activity of a material is defined by [L]- or [D]-, the material is presumed to be achiral or a racemic mixture. The monomer "TMC" is trimethylenecarbonate.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other reference materials mentioned herein are incorporated by reference in their entirety. In case of conflict, the present specification, including definitions, will control. In addition, the materials, methods, and examples are illustrative only and not intended to be limiting.

The invention possesses several distinct advantages. The invention provides high molecular weight, functionalized, bioresorbable copolymers which are sufficiently stable to be thermally processed using a variety of known techniques. This results in a large number of possible forms for materials made of the new copolymers including films, molded products, foams, laminates, spun-bonded nonwoven materials such as filaments, adhesives, and coatings. The new methods allow the creation of polymers which provide increased control over physical properties of functionalized, bioresorbable compositions, including the hydrolytic degradability, melt temperature, and glass transition temperature. The variety of pendant functional groups present in the new copolymers enable a variety of covalent and non-covalent bonding interactions with molecules of biological and pharmaceutical interest, which, in turn, allows the new copolymers to be used to manufacture various drug delivery devices and surgical implants, e.g., timed-release drug compositions. Applications in tissue engineering are also enabled by the new copolymers.

Other features and advantages of the invention will be apparent from the following detailed description and from the claims.

DETAILED DESCRIPTION

Figure 1:
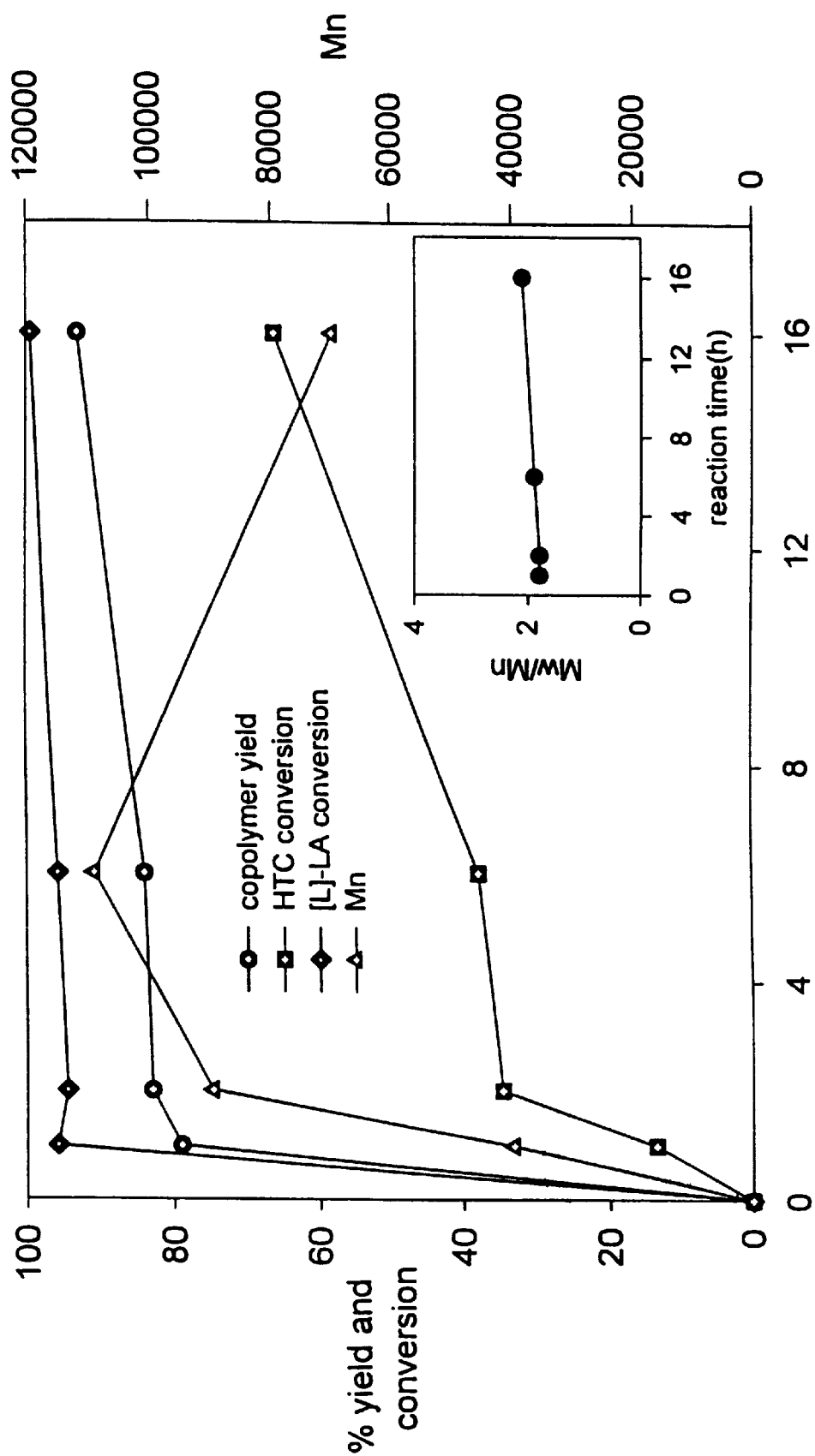
FIG. 1 is a graph showing percentage copolymer yield, conversion percentage of starting comonomers, and the number average molecular weight ($M_n$) and polydispersity of the copolymer as a function of reaction time.

The invention provides a variety of stable, easily-processable, bioresorbable copolymers containing pendant functional groups, or mixtures of such groups in single copolymers or mixtures of copolymers. Bioresorbability is provided through the use of ester and carbonate comonomers. The pendant functional groups provide specific interactions with, for example, many biologically active molecules and cell types for drug delivery and tissue engineering applications.

The new copolymers can be used to prepare copolymer compositions that include homopolymers, copolymers, or physical blends of homopolymers and/or copolymers. Also envisioned are terpolymers and higher order copolymers with mixtures of comonomers containing different functional groups, allowing even greater flexibility in controlling binding characteristics to substrate molecules, i.e., the specific capabilities of different molecules for covalent and/or noncovalent interactions. The copolymers of the present invention are envisioned as random, block, alternating, graft, network, and polyblend copolymers, or mixtures thereof. The copolymers of the present invention can be selected from a variety of nontoxic degradable copolymers. The copolymers of the invention are hydrolytically degradable. It is further considered desirable that the copolymers of the invention be biodegradable and bioresorbable.

The synthetic methods developed to create the copolymers represent a new core technology with great potential for immediate biomedical utility and further development. The attainment of high molecular weights improves the physical properties of the resulting copolymers. Important properties of the new copolymers include tensile strength, modulus, and thermal stability.

Bioresorbable polymers having pendant functional groups are of particular interest, since they are capable of covalent and non-covalent binding. On derivatization of the pendant functional groups, previously unattainable variations in hydrophobicity, macroscopic physical properties, degradability, and chain binding properties can be achieved. Further functionalizations of the copolymers are also possible as described below.

The functional groups contemplated for the new copolymers include alkene, ketal, epoxy, hydroxyl, amine, carboxylate, thiol, ester, and combinations of such groups on single comonomers. Polylactic acid (PLA)-containing comonomers with pendant alkene groups can be cross-linked by free radical reactions during or subsequent to processing. Ketal-functionalized monomers in PLA-based copolymers can function as cross-linking agents for the production of network copolymers with well-defined physical properties. The presence of geminal or vicinal hydroxyl groups of ketal units which are subsequently deprotected promotes strong hydrogen bonding interactions with molecules of biological importance. The epoxy structure in the polymer is readily converted into other functionalities, such as di-hydroxyl, alkoxy-hydroxyl, amine-hydroxyl, and others. The hydroxyl- or epoxy-containing PLAs can be used as macro-initiators for carrying out ring-opening grafting copolymerizations with other functionalized or nonfunctionalized copolymers. One application of these graft copolymers is for the design of improved interfacial agents for bioresorbable blends. In these embodiments, polymers or copolymers grafted onto the new functionalized bioresorbable copolymers can be other functionalized or unfunctionalized bioresorbable copolymers such as lactone-, lactam-, thiolactone-, or N-carboxy anhydride-based copolymers.

Alternatively, the graft ring-opening polymerization of N-carboxyanhydrides (NCA) can be used to introduce peptide side groups. Also, NCA graft ring-opening polymerizations can be initiated by chain functional groups within the pores of foams which contain the new functional copolymers. In this way, the pore structure of new foams are adjustable for optimal interactions with cell colonies.

The new copolymers include two main components referred to as Comonomer I and Comonomer II.

Comonomer I

The first component (Comonomer I) is selected from the following groups: hydroxy carboxylic acids such as α-hydroxy carboxylic acids including lactic acid, glycolic acid, lactide, and glycolide; β-hydroxy carboxylic acids including β-methyl-β-propiolactone; γ-hydroxy carboxylic acids; δ-hydroxy carboxylic acids; and ε-hydroxy carboxylic acids including ε-hydroxycaproic acid; lactones such as: β-lactones; γ-lactones; δ-lactones including δ-valerolactone; and ε-lactones such as ε-caprolactone; benzyl ester-protected lactones such as benzyl malolactone; lactams such as: β-lactams; γ-lactams; δ-lactams; and ε-lactams; thiolactones such as 1,4-dithiane-2,5-dione; dioxanones; unfunctionalized cyclic carbonates such as: trimethylene carbonate, alkyl substituted trimethylene carbonates, and spiro-bis-dimethylene carbonate (2,4,7,9-tetraoxa-spiro[5.5]undecan-3,8-dione); substituted N-carboxy anydrides; polyhydroxybutyrates; and substituted variations, and combinations of the above.

The copolymers can include repeating Comonomer I units of lactic acid, or preferably, intermolecularly esterified dilactic acid, known as lactide. Another useful comonomer is glycolic acid, or preferably, intermolecularly esterified diglycolic acid, known as glycolide. Such repeating units can be constructed by either the polymerization of lactic acid or glycolic acid, or preferably, the ring-opening polymerization of lactide or glycloide to form polylactic acid (PLA) or polyglycolic acid (PGA). Typically, the copolymer includes more than about 25 weight percent repeating units derived from lactide or glycolide, and in some examples, greater than about 50 weight percent. In some lactide-containing embodiments, the poaymer is prepared by polymerization of a composition including lactide in which greater than about 50% by weight of the lactide is optically active and less than 50% is optically inactive, i.e., racemic [D,L]-lactide and meso [D,L]-lactide. In other embodiments, the optical activity of the lactide monomers is defined as [L], and the lactide monomers are at least about 90% optically active [L]-lactide. In still other embodiments, the lactide monomers are at least about 95% optically active [L]-lactide.

In general, linear (unsubstituted) PLA is formed from ring-opening polymerization of the cyclic dimeric ester of lactic acid, i.e., lactide. The precise nature of the polymerization is not fully understood. While not wishing to be bound by any particular theory regarding the reaction mechanism, in general the polymerization mechanism appears to concern chain propagation as presented below. An initiator having a group containing an active moiety (such as an —OH group) is provided and mixed with the lactic acid or lactide. The initiator can include for example, water, an alcohol, lactic acid, amines or other materials. The "active moiety group" reacts with one of the carbonyl groups of the cyclic dimer, to open the lactide ring. Each ring-opening results in the generation of an active —OH group on the end of the polymer backbone. The newly generated active —OH group can react with another lactide molecule, to open its ring. Chain propagation thus occurs in a linear fashion. The lengths of the chains, and thus the molecular weight of the resulting polymer, will, in part, depend on the number of active —OH groups initially provided and the rate of reaction and length of time allowed. If each initiator has only one or two active —OH groups, in general, the resultant product will be a linear polymer with one or two hydroxyl terminated ends. In general, as more equivalents of initiator are provided, the molecular weight of the resulting polymer will be lower. That is, in general, molecular weight is inversely proportional to the number of initiators.

Comonomer II

The second main component of the new copolymers includes repeating monomer or comonomer units derived from functionalized cyclic carbonate monomers. Cyclic carbonate comonomers are considered useful and are shown here and referred to herein as Comonomer II, having the general structural formula:

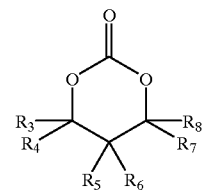

where the R groups can be hydrogen, a variety of substituted or unsubstituted short or medium chain alkyls, including those interrupted by oxygen, nitrogen, or sulfur atoms, including bridged or fused multicyclic groups, but which also contain one or more functional groups, e.g., alkene, alkyne, ester, amide, amine, thiol, thioether, protected hydroxy or polyhydroxy groups found in the form of a ketal, acetal, benzyl ester, or benzyl ether; or combinations of such groups on a single comonomer.

Upon polymerization, the functionalized cyclic carbonate comonomers take the form of polycarbonates, as shown below.

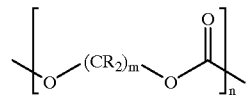

wherein R is hydrogen or any group mentioned above, m can be 1 to 5, and n can be as high as 20,000.

Typically, the copolymer of the present invention includes the above repeating monomer or comonomer units of Copolymer II in an amount of at least 0.5 mole percent, e.g., at least 1.0, 1.5, 2.0, 2.5, or 3.0 mole percent.

The functionalized cyclic carbonate comonomers possess pendant functional groups that enable covalent and/or non-covalent interactions with other molecules. Such other molecules can be either biologically active or not biologically active. Alternatively, such other molecules can be fully or partially formed copolymers of variable composition. This type of architecture enables the construction of network copolymers of controlled structure and composition, resulting in materials of defined physical properties and binding characteristics.

The functional groups pendant from the comonomer can be further manipulated after copolymerization to obtain desirable physical properties and binding characteristics. The protected hydroxyl groups in the form of ketals, acetals, benzyl esters, and benzyl ethers can be deprotected subsequent to polymerization to yield hydroxyl groups in the copolymer.

One of the contemplated second, functionalized comonomers of the new copolymers is referred to here as HTC. HTC is the cyclic carbonate monomer 2,4-dioxaspiro[5.5] undecane-8-ene-3-one and has the following structure:

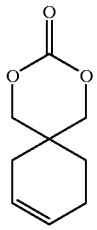

Copolymers with HTC content of >52 mol % are expected to have $T_g$ values that are below normal body temperature. Modulation of the $T_g$ above and below that of normal physiological temperatures represents a method for regulation of physical properties and bioresorption rates. It is found that $T_g$ varies inversely with concentration of HTC. Thus, the HTC homopolymer has a $T_g$ of about 32° C.; 25% HTC in a polylactide copolymer has a $T_g$ of about 55° C.

Further, the new copolymers can contain alkene pendant groups in the range of from 0.1% up to 95%. A useful range is from 0.5% to 75%, e.g., from 1% to 50%. The crystallinity is also expected to vary with variations in [D]-PLA content. Copolymers with lactide having variable [D]- and [L]-PLA content are envisioned.

Besides providing control over the macroscopic physical properties of resulting copolymers, copolymers with alkene pendant groups or substituents also provide a number of opportunities for further copolymer modification and functionalization. For example the transformation of copolymer alkene substituents to epoxides, e.g., using peroxy acids, ultimately results in trans-1,2-diols, trans-α-hydroxy ethers, by oxirane ring opening, and other difunctionalized copolymers, according to known methods of —OH derivitization. Pendent alkene substituents can also result in cis-1,2-diols through other transformations involving known syntheses and reagents.

The conversion of alkenes to epoxides is carried out by using peroxyacids known in the art. Such acids include peroxybenzoic acids such as peracetic acid, monoperphthalic acid, pertrifluoric acid, performic acid, 3-chloroperoxybenzoic acid, or t-butylperoxybenzoic acid, or their alkali metal salts. Such reactions may be catalysed, for example by cuprous salts. The products of these reactions are the epoxides, which are hydrolysed to yield trans glycols. Cis-hydroxylation is also available through the use of other reagents and conditions, for example, dilute potassium permanganate, or osmium tetroxide with or without chlorate in dioxane, followed by treatment with mannitol. Iodine and silver acetate in wet acetic acid also give cis-hydroxides in good yields.

Copolymers containing alkene substituents can also be crosslinked with other alkene-containing copolymers, thereby creating network polymers. Large increases in crosslinking increases the rigidity, softening point, and modulus of polymers, and reduces elongation and swelling by solvents. Largely crystalline polymers can be affected differently by small increases in crosslinking. The presence of a few crosslinks can reduce crystallinity by reducing chain orientation, changing a high-melting, hard, dense crystalline polymer to a more elastic, softer material.

Crosslinking of unsaturated copolymers takes place through abstraction of one of the allylic hydrogens by a radical initiator. Examples of such initiators are peroxides, perbenzoates, and 2-phenylazoalkylnitriles. They are generally present in amounts of approximately 1 to 5 percent by weight, e.g., 2 or 3 percent. Subsequent steps in the crosslinking involve attack by the polymer-based radical of a double bond in a second polymer chain, producing a crosslink and another polymer radical. The process is terminated by reaction of the polymer-based radical with the radical initiator.

In this way, the new functionalized copolymers can be crosslinked with each other to form more rigid copolymers or more elastic copolymers, depending on the degree of crosslinking introduced. Alternatively, the new functionalized copolymers can be crosslinked with other crosslinkable materials such as alkene-containing biodegradable copolymers.

Some of the functionalized copolymers of the invention are constructed using ketal-protected, cyclic carbonate comonomers. The resulting copolymers contain ketal groups which can act as intermediates to hydroxyl-containing copolymers. Removal of the ketal groups must be accomplished subsequent to copolymerization, since the presence of hyroxyl groups would be detrimental to copolymerization. Removal of ketals is done under acidic conditions ($CF_3COOH/H_2O$ or $BCl_3$) to yield PLA-based copolymers with pendant dihydroxyl groups. Copolymers containing comonomers with pendant dihydroxyl groups are useful in that form, as described above, or can be further functionalized to obtain a variety of other functionalized copolymers. Examples of such include hydroxy/amines, hydroxy/ethers, diamines, diethers and other such difunctional copolymers prepared by known methods and with known reagents.

Specific examples of such ketal-containing cyclic carbonate Comonomers II useful in the present invention are those defined here as IPXTC and DMTOS. IPXTC is the cyclic carbonate monomer 1,2-O-isopropylidene-D-xylofuranose-3,5-cyclic carbonate and has the following structure:

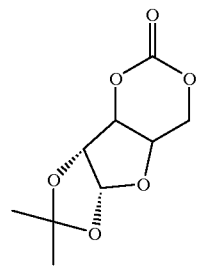

Variations in the amount of IPXTC in PLA copolymers result in variations in the $T_g$. Thus, while the homopolymer of PLA has a $T_g$ of about 60° C., a 60 mol % IPXTC-containing copolymer with PLA has a $T_g$ of about 90° C.

Another specific example of a ketal protected structure II cyclic carbonate is DMTOS, the cyclic carbonate monomer 9,9-dimethyl-2,4,8,10-tetraoxaspiro[5.5]undecane-3-one having the following structure:

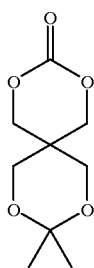

Copolymer Physical Properties

Copolymers of the invention can be random copolymers, alternating copolymers, graft copolymers, or block copolymers, depending on the properties of the polymer required for the particular application. Illustrative of useful copolymers are random copolymers comprising one or more monomeric units of each of the comonomers corresponding to Comonomers I or II described herein.

Also illustrative of copolymers useful in the compositions of the invention are block copolymers comprising one or more "B" blocks which can be formed of recurring units of Comonomer I and one or more "A" blocks which can be formed of recurring units of Comonomer II. Each "A" block and each "B" block can be the same or different. A "block" is a sequence of one type of monomeric unit at least 5 monomeric units long, or a sequence of two or more types of recurring monomeric units either randomly distributed in such a sequence or distributed in such a sequence in a block-like fashion. Each "A" block and "B" block can include a single type of recurring monomeric unit. Alternatively, each block can include more than one type of recurring monomeric unit, randomly distributed throughout each block.

For example, the block copolymers described above can have repeating block units such as AB, ABA, BAB, ABAB, ABABA, BABAB, and the like, where each "A" block and each "B" block contains the same or substantially the same number of recurring units. Alternatively, the various "A" and "B" blocks contained in the block copolymers can have more thani one type or types of recurring monomeric units; or each block can contain the same or different types of recurring units, but have a differing number of recurring units in each block. With respect to the recurring blocks of A's and B's, each of them can also be the same or different. For example, ABABA can be in fact MNOPQ, BAB can be MNQ, or ABA can be MNOPQ, where M, N, O, P and Q are the same or different, provided that at least one of M, N, O, P and Q is a recurring unit of the Comonomer I and another is a unit of Comonomer II.

The new copolymers are designed to display physical properties appropriate for use in processing requirements. Useful properties are a tensile strength of at least 9000 psi and up to 10,000 and 15,000 psi or more, an elongation to failure of from 5 to 200 percent, e.g., 30 to 120 or 500 to 100 percent, a tangent modulus of at least $6 \times 10^5$ psi and up to $10^6$ and $10^7$ psi, and thermal stability up to 350° C.

Typically, the copolymer should have a weight average molecular weight of between 4,000 and 1,500,000. Another useful range is between 20,000 and 900,000. A further useful range is between 60,000 and 600,000. Appropriate molecular weights of copolymers in accordance with the parameters of the present invention can be achieved by varying the copolymerization temperature, comonomer ratios, and catalyst as discussed below.

The molecular weight distributions are characterized by a polydispersity value ($M_w/M_n$). $M_n$ is the number average molecular weight of a polymer and is defined by the weight of a given sample of polymer divided by the number of molecules within that sample. $M_w$ is the weight average molecular weight and is defined by the summation of the product of the molecular weight of the species, squared, and the number of molecules of the species, divided by the summation of the product of the molecular weight of the species and the number of molecules of the species. Copolymers useful for the purposes of the new compositions have polydispersity values of between 1.03 and 10.00. Another useful range is between 1.2 and 5.0, as well as between 1.4 and 3.0.

The new copolymers can be used in diverse concentrations to prepare a variety of different compositions. Useful compositions can be made of 100 percent of new copolymers, or they can include low amounts of the new copolymers, with the balance of the composition being unfunctionalized bioresorbable copolymer. Preferably, the compositions include a high enough percentage of hydrolytically degradable copolymer segments so that, upon degradation, polymer fragments of less than about 600 molecular weight units are produced, because such polymer fragments are small enough to be metabolized by microorganisms.

Copolymers with repeat units containing hydroxyl groups impart unique properties to the new copolymers that allow for a variety of potential applications. For example, substrates can be covalently bound to the hydroxyl groups of the new copolymers. Alternatively, linear and crosslinked hydroxyl-containing polyesters can permit the formation of strong hydrogen bonding interactions with organic and inorganic species. Thus, contacting new copolymers which contain hydroxyl groups with molecules which can form hydrogen bonding interactions with these groups such as proteins, glycoproteins, and peptides can result in compositions in which the molecules are encapsulated or substantially encapsulated by the new copolymers. Introduction of these compositions into organisms by a variety of means results in time-release of those molecules through biodegradation and bioresorbtion. Hydroxyl groups could interact with or bind to bioactive molecules, with similar implications for encapsulation and time-release.

In addition, the existence of the hydroxyl groups enhances the hydrolytic degradability of the polymer. The hydrophobicity of hydroxyl-containing copolymers is greatly reduced, and water molecules associated with the inner hydration shell of such copolymers can assist hydrolytic degradation via the nucleophilic attack of water at ester linkages.

Crosslinking of hydroxyl-containing copolymers can take place through any of the methods known for crosslinking such materials as cellulose, including treatment with formaldehyde or other aldehydes, epoxides or diepoxides, or certain non-toxic sulfones, such as bis(2-hydroxyethyl) sulfone. Isocyanates or anhydrides can also be used to crosslink hydroxyl-containing copolymers.

Copolymers containing pendant alkene functionalities are of considerable interest. Variations in the alkene-containing functional group content in the polymers of the present invention are useful in influencing the glass transition temperature ($T_g$), melting transition temperature, and enthalpy of fusion. Modulation of polymer thermal properties by such copolymerizations can be exploited to improve copolymer processability relative to lactide homopolymer and to increase polymer hydrolytic degradability relative to highly crystalline PLA materials. As shown in Example 3, increases in the HTC content of PLA-based copolymers decrease the glass transition temperature of the new copolymers. Conversion of alkene pendant groups to hydroxyl pendant groups via epoxidation increases the hydrolytic degradability of the new copolymers.

Copolymer Preparation

The new copolymers can be prepared by a variety of polymerization techniques, including bulk polymerization, suspension polymerization, and solution polymerization, e.g., ring-opening polymerization. Preferably, the polymerization reaction is conducted in the liquid phase in a closed, evacuated vessel. Alternatively, the polymer can be prepared at atmospheric pressure with the polymerization mixture blanketed by an inert gas such as, for example, nitrogen or argon. If the polymerization is conducted in the presence of oxygen or air, some discoloration can occur with a resulting decrease in molecular weight and tensile strength.

Typically, the polymerization is conducted at a temperature above the melting point of the monomers or comonomers and below a temperature at which degradation of the resulting polymer occurs. For example, in the case of production of polylactic acid from the polymerization of L-lactide and/or D,L-lactide, the polymerization can be conducted at a temperature of between 100° C. and 170° C, e.g., between 100° C. and 150° C., or between 120° C. and 140° C.

The ring-opening copolymerization discussed above can employ a catalyst. Such catalysts are chosen from the broad family of organometallic reagents that chelate and promote ring-opening reactions of the monomers discussed herein. These catalysts generally either open one of the carbon-heteroatom bonds directly or form a complex with a ring, thereby facilitating the opening of the ring by the functional group of another comonomer. Examples of catalysts that can be employed in the methods of the present invention are $AlR_3$ (R=ethyl, isobutyl, secbutyl, or isopropoxyl) $ZnEt_2$-$H_2O$, $Sn(Oct)_2$, $Sn(C_6H_5)_4$, $La(OR)_3$, $Y(OR)_3$ (R=ethyl, isobutyl, secbutyl, or isopropoxyl), or other suitable copolymerization catalyst, such as other lanthanide-alkane complexes and bimetallic reagents.

Catalysts are used in normal catalytic amounts for polymerization. For example, a stannous octoate catalyst concentration in a range of 0.001 to 1.0 percent by weight, based on total weight of the monomers or comonomers, is suitable. A catalyst concentration in the range of 0.01 to 0.1 percent by weight is useful. The exact amount of catalyst in any particular polymerization system depends to a large extent upon the catalyst employed and the operating variables, including time, temperature, and the desired rate of reaction.

The reaction time of the polymerization is dependent on other reaction variables, including reaction temperature, polymerization catalyst, amount of catalyst, degree of mixing, and whether a solvent is used. The reaction time can vary from a matter of minutes to a period of hours or days, depending on the particular set of conditions which is employed. Heating of the mixtures of monomers or comonomers is continued until the desired level of polymerization is attained. For example, the reaction temperature can be chosen so that the polymerization is stopped prior to complete reaction of all monomers or comonomers to provide for a polymer composition having residual comonomers. Reaction temperatures can range from 100° C. to 140° C.; e.g., between 110° C. and 120° C.

The reaction can be halted at such time that the polymer composition has the desired degree of conversion to attain the desired level of residual monomer and comonomer. In a preferred embodiment of the present invention, less than approximately 0.5% by weight of monomer or comonomer is left unreacted.

In general, it is preferred to conduct the polymerization in the absence of impurities which contain active hydrogen, because the presence of such impurities tends to deactivate the catalyst and/or increase the reaction time. It is also preferred to conduct the polymerization under inert atmosphere and anhydrous conditions.

The polymerization can be carried out in the presence of an inert, normally liquid organic vehicle such as, for example, aromatic hydrocarbons, e.g., benzene, toluene, xylene, or ethylbenzene; oxygenated organic compounds such as anisole, dimethyl and diethyl esters of ethylene glycol; normally liquid, saturated hydrocarbons including open-chain, cyclic, and alkyl-substituted hydrocarbons such as hexane, heptane, cyclohexane, or decahydronaphthalene. Likewise, the polymerization can be carried out in the absence of added solvent.

The polymerization process can be conducted in a batch, semi-continuous, or continuous manner. In preparing the monomeric reactants and catalysts for subsequent polymerization, they can be admixed in any order according to known polymerization techniques. Thus, the catalyst can be added to one comonomeric reactant. Thereafter, the catalyst-containing comonomer or copolymer product can be admixed with another comonomer. In the alternative, comonomeric reactants can be admixed with each other. The catalyst can then be added to the reactant mixture. If desired, the catalyst can be dissolved or suspended in an inert, normally liquid organic vehicle. If desired, the monomeric reactants can be added to the catalyst, catalyst solution, or catalyst suspension either as a solution or a suspension in an inert organic vehicle.

The catalyst and comonomeric reactants also can be added to a reaction vessel simultaneously, and the polymerization can be conducted in the presence of a preformed polymer. The reaction vessel can be equipped with a conventional heat exchanger and/or mixing device. The reaction vessel can be any equipment normally employed in the art of making polymers. One suitable vessel, for example, is a stainless steel vessel.

Other additives can be employed in the preparation of copolymer compositions. For example, inclusion of other copolymers, functionalized as in the present invention, is contemplated. Alternatively, other functionalized bioresorbable copolymers can be added. Non-functionalized bioresorbable copolymers such as PLA or poly(glycolide) (PGA) can be utilized. Various plasticizers, crosslinking agents, pigments, fillers, antioxidants, UV light absorbers, bactericides, fungicides and other additives known in the art can also be used.

Processing

The present invention includes various compositions made from the new copolymers and various additives. The compositions have varying chemical and physical characteristics which are relevant to their intended uses. The compositions can be processed to form a variety of products including films, molded products, laminates, foams, spun-bonded nonwoven materials such as filaments, adhesives, and coatings.

For example, the compositions can be used to make films. Films typically have thicknesses of less than about 20 mil but can have thicknesses up to about 50 mil. Such films can be prepared to simulate the properties of common materials, such as polyethylenes, polystyrenes, and other poly(vinyls). The desired molecular weight distribution for each application is achieved by adjustment of the polymerization conditions and by post-polymerization processing. Such films can be produced by a variety of known processes, such as compression molding. Suitable films can also be prepared by extrusion processes, including blown film processes, melt-extruded casting, and by casting solutions of the polymer composition and then recovering the solvent. The morphologies of the films are controlled by thermal annealing and quenching according to methods known to the art.

The new films can be oriented or not and can be shrinkable or not. Orientation refers to stretching a film in one direction which allows for alignment and ordering of the polymer molecules along the direction of stretching. Films can be biaxially oriented by stretching the film in the direction the film travels as it is processed and in a second direction transverse to the first. Biaxially oriented films are useful as shrinkable films for various applications. The shrinkability of biaxially oriented films is introduced by heat setting the films by techniques known to the art.

The new compositions can also be used to prepare various molded products. Molded products can be made by a variety of processes including blow molding, injection molding, and thermoforming. For example, blow molding can be employed to make hollow shapes.

Injection molding is accomplished by melting the composition and transferring it to a mold cavity where it solidifies to conform to the shape of the mold. The materials of the present invention are highly suitable for injection molding because their melting points and morphologies can be tailored in many different ways. The melt rheology of the materials can be adjusted by variations in molecular weight and distribution, degree of crosslinking, and comonomer identity and amount to tailor the melt viscosity, shear dependence, heat-deflection temperatures, crystallization temperature, and other processing requirements.

Thermoforming is a branch of molding that uses films or sheets of thermoplastic. Because the new materials are especially easy to convert to film or sheet form, they are excellent candidates for thermoforming. The sheet must be heated to the temperature at which it is quite flexible and then subjected to vacuum or pressure that presses the sheet against a mold, forming the desired shape.

The new compositions can also be processed to form laminates and coextrudates. Film laminates and coextruded films are composite materials in which each layer provides functional utility that complements the rest of the structure. The compositions can also be used to form laminating resins that can be used as tie-layers between dissimilar surface layers. Such laminated materials, for example, have layers that perform various functions, such as structural stability, gas permeability, and moisture exclusion.

In addition, the compositions can be used to manufacture foams. The compositions are excellent candidates for use in the production of foams because they can be melted to a high-viscosity material that can be blended with such gases as carbon dioxide or nitrogen for foam extrusion. The viscosity of the melt can be optimized by controlling the molecular weight, molecular weight distribution, degree of crosslinking, and by additive content.

The new compositions can also be used to form spunbonded nonwoven material. This material is prepared by extruding a filament through a spinnerette onto a flat cooled surface in an irregular pattern to form a relatively uniform sheet which is not in a woven pattern. This requires the use of a limited range of melt viscosities so that the roving spinnerettes can deliver the appropriate amount of material to the cooled surface. Additives play an important role by facilitating the initial bonding among fibers, and the fiber pliability.

The new compositions can also be processed to form adhesives. The polymer compositions of the invention have considerable utility as adhesives because they can be hot-melt or solvent-based products. Choice of comonomers and the molecular weight distribution can affect the melting point of the hot melt and its changes in morphology during tackifying and hardening. The excellent compatibility of the new carbonate-based copolymers and other new copolymers with substances with solubility parameters that differ widely among themselves indicates that these polymers are especially suited to bonding together disparate materials.

The compositions can also be used to prepare various coatings. Unlike some films, moldings, and foams, coatings do not have to be strong enough to be self-supporting. Therefore, an extremely wide range of the new copolymer compositions can be used for coating. The degradability aspect allows the coating to be a temporary protection of the underlying substrate against abrasion or other harm. The coating can serve many of the functions of a film.

Although the new compositions are hydrolytically degradable and further bioresorbable, they also can be treated by other disposal systems. In particular, they can be incinerated in facilities that burn other plastic wastes. They also can be recycled with other thermoplastics by blending.

Methods of Use

The copolymers can interact with substrates in many different ways. For example, the copolymer can interact with a bioactive substrate, or a bioinert substrate, either by covalent or noncovalent bonding. Noncovalent interactions include hydrogen-bonding interactions, hydrophobic interactions, and interactions that take place through the intervention of solvent molecules, especially water. Alternatively, the interactions could occur directly through the functional groups of the copolymer. However, the specific juxtapositional relationship of the copolymers and the substrates is not critical to the invention.

The new copolymers and copolymer compositions can be used for a wide variety of applications. Some of these applications are in the biomedical fields. These applications include, but are not limited to, the construction of medical devices which can contain drugs useful for healing, medication, or disease prevention. Methods of delivery of such devices include oral administration, injection, or surgical implantation. The devices can take the form of films, sheets, foams, or solid objects of any shape, as discussed above.

The substrates envisioned for use in the present invention can be pharmaceutically active, or can become pharmaceutically active as a result of transformations that take place in organisms. Among these substrates are compounds and other materials regarded as drugs. The drugs contemplated for delivery by the copolymers of the invention include, e.g., insulin, anticancer drugs, and proteins.

Another area of biomedical application is in the field of tissue engineering. The compositions of the present invention allow the growth of different types of cells, such as endothelial cells, on surfaces coated with the new functionalized bioresorbable copolymers.

The substrates can be contacted with the new copolymers by dispersion in a copolymer matrix. This can involve any process or reaction leading to covalent or noncovalent binding of the substrate to the copolymer.

Another important advantage of this invention is the greatly reduced volume of the drug necessary compared to standard liquid drug dispensing devices. Solid drug compositions occupy a very small volume in comparison with liquid drug formulations. With many drugs, this reduces the total volume by hundreds of thousands of times, and thus would allow a drug-dispensing device to be much smaller than drug delivery devices, such as pumps, designed to dispense liquids.

The invention will be further described in the following examples, which illustrate the invention, and do not limit the scope of the invention described in the claims.

EXAMPLES

The following examples illustrate preparation and processing methods as well as properties of various copolymers of the invention.

Example 1
Preparation of Catalysts

To a previously silanized and flame-dried 10 mL Schlenk tube, 1 mL $ZnEt_2$ (1.1 M in toluene) was injected via syringe. The tube was kept under inert atmosphere. The solution was cooled in an external dry ice/acetone bath followed by slowly adding with vigorous stirring a 1,4-dioxane solution (99 µL) containing 9.9 µL distilled water. After 15 minutes, the cooling bath was removed and the temperature was increased to 25° C. The resulting clear solution was stored at about 4° C. for up to two weeks prior to use without loss of catalytic activity. Solutions (1 mol/L) of $Al(O\text{-isopropyl})_3$ and $Sn(Oct)_2$ were prepared similarly, but in dry toluene.

Example 2
General Procedure for Copolymerization

Polymerization ampules (10 mL) were treated with trimethylsilyl chloride, washed with three 5 mL portions of methanol, dried at 100° C. in an oven and flame-dried while purging with dried argon. The desired monomer (0.5 to 5.0 g) and the catalyst solution (0.3 mL of $3\times10^{-5}$ M) were transferred into the ampule using a glovebox to maintain an inert nitrogen atmosphere. The ampule was then sealed under argon and placed in a heated oil bath for a predetermined reaction time. At the end of the reaction period, the contents of the ampule were dissolved in chloroform (8 mL), the chloroform solution was added to methanol (80 mL) to precipitate the polymer, the precipitate was washed with several portions of methanol and then volatiles were removed in a vacuum oven (<3 mmHg, 40° C., 24 hours).

An increase in temperature for a given monomer feed ratio is seen to both increase the overall yield of copolymer and increase the HTC content of the copolymer. Molecular weights of the resulting HTC-[L]-LA copolymers are maximized at copolymerization temperatures of about 120° C. and can reach over 100 KDa with $Sn(Oct)_2$ (stannous octoate) as catalyst. The polydispersity of the copolymers is dependent on the catalyst used. Polydispersity of PLA-HTC copolymers using aluminum catalysts shows values of around 1.4–1.7, whereas use of $Sn(Oct)_2$ gives values of 1.9–2.7 and use of $ZnEt_2$-$H_2O$ gives values of 2.2–2.3.

TABLE 1

| entry | catalyst | $f_{PLA}/f_{HTC}$ | temp (° C.) | yield (%) | $M_n$ (Da) | $M_w/M_n$ | $F_{PLA}/F_{HTC}$ |
|---|---|---|---|---|---|---|---|
| 1 | $AlEt_3$-0.5$H_2O$ | 83/17 | 120 | 77 | 34000 | 1.5 | 96/4 |
| 2 | $AlEt_3$-0.5$H_2O$ | 67/33 | 120 | 67 | 26100 | 1.7 | 90/10 |
| 3 | $Al^iBu_3$-0.5$H_2O$ | 82/18 | 120 | 67 | 47800 | 1.7 | 97/3 |
| 4 | $Al^iBu_3$-0.5H2O | 66/34 | 120 | 54 | 21700 | 1.4 | 94/6 |
| 5 | $Al(OPr)_3$ | 81/19 | 120 | 78 | 34900 | 1.7 | 95/5 |
| 6 | $Al(OPr)_3$ | 65/35 | 120 | 70 | 24700 | 1.7 | 88/12 |
| 7 | $Sn(Oct)_2$ | 82/18 | 100 | 81 | 72300 | 2.1 | 95/5 |
| 8 | $Sn(Oct)_2$ | 82/18 | 120 | 84 | 109000 | 1.9 | 92/8 |
| 9 | $Sn(Oct)_2$ | 82/18 | 140 | 88 | 54200 | 2.7 | 88/12 |

TABLE 1-continued

| entry | catalyst | $f_{PLA}/f_{HTC}$ | temp (° C.) | yield (%) | $M_n$ (Da) | $M_w/M_n$ | $F_{PLA}/F_{HTC}$ |
|---|---|---|---|---|---|---|---|
| 10 | $Sn(Oct)_2$ | 67/33 | 120 | 68 | 82200 | 2.1 | 86/14 |
| 11 | $ZnEt_2$-0.5$H_2O$ | 83/17 | 120 | 82 | 49400 | 2.3 | 95/5 |
| 12 | $ZnEt_2$-0.5$H_2O$ | 67/33 | 120 | 68 | 45700 | 2.2 | 88/12 |

The content of alkene pendant groups in the copolymer can be controlled through variations in the LA/HTC comonomer feed ratio. This is shown in Table 2. Stannous octoate $(Sn(Oct)_2)$ was used as the catalyst, copolymerization was carried out at 120° C. for 6 hours, with a comonomer/catalyst ratio of 200:1. Molecular weight and yield values were determined as described immediately prior to Table 1. Satisfactory yields and favorable number average molecular weights (ca. 100 kDa) are obtained with comonomer feed ratios of approximately 4:1 PLA/HTC, resulting in approximately 10 mol % alkene functionalization of the copolymer.

TABLE 2

| entry | $f_{PLA}/f_{HTC}$ | yield (%) | $M_n$ (Da) | $M_w/M_n$ | $F_{PLA}/F_{HTC}$ |
|---|---|---|---|---|---|
| 13 | 0/100 | 91 | 55700 | 2.0 | 0/100 |
| 14 | 30/70 | 43 | 35300 | 1.9 | 48/52 |
| 15 | 49/51 | 47 | 49800 | 2.2 | 72/28 |
| 10 | 67/33 | 68 | 82200 | 2.1 | 86/14 |
| 16 | 82/18 | 82 | 99700 | 2.0 | 93/7 |
| 17 | 100/0 | 99 | 86000 | 2.1 | 100/0 |

As shown in FIG. 1, PLA-HTC copolymer yield, HTC conversion, PLA conversion, $M_n$, and $M_w/M_n$ were monitored over 16 hours of reaction time. The number average molecular weights maximize at approximately 6 to 8 hours reaction time. Increases in the polydispersity values, to over 2.0, are also observed after this reaction time for HTC-[L]-LA copolymers as shown.

Example 3
$T_g$ of HTC-Containing Copolymers

The glass transition temperature of various HTC-containing copolymers was determined. The values are presented in the following Table 3.

TABLE 3

| $F_{HTC}$ | $T_g$ (° C.) |
|---|---|
| 100% | 32 |
| 50% | 41 |
| 25% | 54 |
| 12% | 55 |
| 6% | 56 |

Example 4
Converting Alkenes to Epoxides

A copolymer with 14 mol % alkene repeat units (HTC-containing) was selected for illustration of the conversion of alkene substituents to epoxides (entry 10 in Table 1). The epoxidations were performed by using a 1:1 molar ratio of alkene to 3-chloroperoxybenzoic acid at room temperature. Epoxidation reaction efficiency was determined from the relative intensity of the epoxide and alkene $^1$H-NMR signals at 3.15 and 5.5–5.8 ppm, respectively. The molecular weights presented are those of the resulting epoxidized product and were determined as described prior to Table 1.

The %-conversion of vinyl to epoxy groups was about 35% for reactions conducted for 0.5 and 1 hour. However, by increasing the reaction time from 1 to 4 hours, the %-conversion increased from 36 to 71%. The apparent molecular weight decreased only slightly during the epoxidation reaction from about 62 kDa to about 59 kDa. See Table 4.

TABLE 4

| entry | reaction time | $M_n$ (Da) | $M_w/M_n$ | vinyl %-conversion |
|---|---|---|---|---|
| epoxy-1 | 0.5 | 67800 | 2.0 | 33 |
| epoxy-2 | 1 | 61900 | 1.8 | 36 |
| epoxy-3 | 4 | 58800 | 1.9 | 71 |

Example 5

IPXTC Synthesis

To a 2.5 L flask immersed in a 0° C. ice bath, 2 liters tetrahydrofuran (THF), 0.8 mol ethyl chloroformate and 0.4 mol 1,2-O-isopropylidene-D-xylofuranose were added. 0.8 mol of diethylamine was added dropwise into the solution with magnetic stirring over a period of 30 minutes. The reaction mixture was maintained at 0° C. for another 1.5 hours with stirring. Then the formed solid (tetraethylammonium chloride) was filtered off and washed with THF. The solution was then dried by rotory evaporation at room temperature. 500 mL of ether was added and the mixture kept at 0° C. overnight. IPXTC was crystallized in ether solution and separated by filtration. The crude IPXTC was recrystallized by THF/ether once again to obtain needle-like, white crystals with a 41% yield.

The effects of different catalysts, comonomer feed ratio ($f_{PLA}/f_{IPXTC}$) and reaction temperature on the IPXTC-[L]-LA copolymer yield, molecular weight and composition ($F_{PLA}/F_{IPXTC}$) are shown in Table 5. The comonomer feed ratios are expressed as mol %. Copolymerizations were carried out for 6 hours, with a comonomer/catalyst ratio of 200:1. The number average ($M_n$) and weight average ($M_w$) molecular weights were determined by standard, refractive index-detection gas phase chromatography in chloroform at room temperature, with polystyrene serving as the internal standard. The yield of copolymer was based on the amount of methanol insoluble copolymer recovered after reaction. The copolymer composition is expressed in mol ratio, and was determined by $^1$H-NMR.

An increase in temperature for a given monomer feed ratio is seen to increase both the overall yield of copolymer and the IPXTC content of the copolymer (compare entries 4 and 10; entries 5 and 9; entries 11 and 12). Molecular weights of the resulting IPXTC-[L]-LA copolymers are maximized at copolymerization temperatures of about 120° C. and reach up to 78 KDa.

TABLE 5

| entry | catalyst | $f_{PLA}/f_{IPXTC}$ | temp. (° C.) | yield (%) | $M_n$ (Da) | $M_w/M_n$ | $F_{PLA}/F_{IPXTC}$ |
|---|---|---|---|---|---|---|---|
| 1 | AlEt$_3$-0.5H$_2$O | 70/30 | 120 | 65 | 20,900 | 1.5 | 87/13 |
| 2 | Al$^i$Bu$_3$-0.5H$_2$O | 72/28 | 120 | 46 | 20,400 | 1.2 | 92/8 |
| 3 | Al(O$^i$Pr)$_3$ | 69/31 | 120 | 68 | 20,900 | 1.5 | 86/14 |
| 4 | Sn(Oct)$_2$ | 82/18 | 100 | 75 | 62,000 | 2.1 | 95/5 |
| 5 | Sn(Oct)$_2$ | 72/28 | 100 | 68 | 52,400 | 1.6 | 93/7 |
| 6 | Sn(Oct)$_2$ | 66/34 | 120 | 70 | 44,500 | 2.0 | 85/15 |
| 7 | Sn(Oct)$_2$ | 71/29 | 120 | 71 | 64,500 | 1.7 | 91/9 |
| 8 | Sn(Oct)$_2$ | 83/17 | 120 | 82 | 78,400 | 1.9 | 93/7 |
| 9 | Sn(Oct)$_2$ | 72/28 | 140 | 83 | 32,400 | 2.0 | 81/19 |
| 10 | Sn(Oct)$_2$ | 82/18 | 140 | 83 | 70,200 | 2.3 | 92/8 |
| 11 | ZnEt$_2$-0.5H$_2$O | 73/27 | 100 | 22 | 29,900 | 1.8 | 92/8 |
| 12 | ZnEt$_2$-0.5H$_2$O | 73/27 | 120 | 68 | 31,900 | 2.0 | 88/12 |
| 13 | ZnEt$_2$-0.5H$_2$O | 71/29 | 140 | 68 | 28,800 | 1.8 | 89/11 |

The relative amounts of ketal-containing pendant groups in the copolymer were controlled through variations in the LA/IPXTC comonomer feed ratio, as shown in Table 6.

Copolymerizations were carried out at 120° C., for 6 hours, except for the case of entries 16 and 17, which were carried out for 24 hours. The catalyst was stannous octoate (Sn(Oct)$_2$), with a comonomer/catalyst ratio of 200:1. The reactions were carried out in bulk, except for the case of entry 17, to which was added 0.5 mL 1,4-dioxane/g IPXTC as solvent. Copolymer yields, number average and weight average molecular weights were determined as described prior to Table 1, except for entry 17, for which some of the values were not determined.

TABLE 6

| entry | $f_{PLA}/f_{IPXTC}$ | yield(%) | $M_n$ (Da) | $M_w/M_n$ | $F_{PLA}/F_{IPXTC}$ |
|---|---|---|---|---|---|
| 14 | 100/0 | 99 | 86,000 | 2.1 | 100/0 |
| 8 | 83/17 | 82 | 78,400 | 1.9 | 93/7 |
| 7 | 71/29 | 71 | 64,500 | 1.7 | 91/9 |
| 6 | 66/34 | 70 | 44,500 | 2.0 | 85/15 |
| 15 | 52/48 | 54 | 27,900 | 1.6 | 79/21 |
| 16 | 36/64 | 48 | 13,900 | 1.7 | 61/39 |
| 17 | 16/84 | 6 | — | — | — |

Example 6

Deprotection of Ketal Groups

Copolymer prepared with ketal-containing comonomers (0.1 g) was dissolved in 0.8 mL of CH$_2$Cl$_2$. To this solution was added either 0.8 mL CF$_3$COOH/0.16 mL distilled H$_2$O or 0.3 mL BCl$_3$ (1 M in CH$_2$Cl$_2$). After stirring at room temperature for 20 minutes in the case of CF$_3$COOH, or 4 minutes in the case of BCl$_3$, the resulting polymeric product was precipitated from solution by adding methanol (80 mL). The polymer was separated by filtration and dried in vacuum to constant weight.

The mol % of remaining ketal was determined by monitoring the $^1$H-NMR signal at 1.33 and 1.53 ppm in the case of IPXTC-derived copolymers. The resulting quantitative analysis of the deprotection of the ketal groups is presented in Table 7.

TABLE 7

| entry | starting polymer | deprotection reagent | mol-% remaining ketal |
|---|---|---|---|
| DP-1 | entry 8, table 1 | CF$_3$COOH/H$_2$O, 20 minutes | 29 |
| DP-2 | entry 12, table 1 | CF$_3$COOH/H$_2$O, 20 minutes | 21 |
| DP-3 | entry 9, table 1 | CF$_3$COOH/H$_2$O, 20 minutes | 37 |
| DP-4 | entry 8, table 1 | BCl$_3$, 4 minutes | ~0 |
| DP-5 | entry 12, table 1 | BCl$_3$, 4 minutes | ~0 |
| DP-6 | entry 9, table 1 | BCl$_3$, 4 minutes | <10 |

Example 7
IPXTC Homopolymerization

Three kinds of catalysts, i.e., typical coordination catalysts, typical anionic catalysts, and rare earth catlysts, were screened for the homopolymerization of IPXTC and the results are summarized in Tables 8 and 9. In Tables 8 and 9, "MAO" is methylaluminoxane, "IBAO" is isobutyl aluminoxane, and "DOX" is dioxane. The "$[\alpha]$" measurement is the optical rotation of the sample of 25° C. and at 589 nm. "Time" is the time of polymerization in hours. "IPXTC/Y" is the monomer to catalyst ratio.

several minutes. In contrast, the polymerization of IPXTC gave only 10% conversion after 25 minutes of polymerization, and 44% conversion after 3 hours of polymerization. This much slower polymerization is ascribed to the lower activity of IPXTC monomer due to the substituents on the six-membered ring, especially the substituent on the carbon vicinal to the oxygen atoms. At the beginning of the polymerization, the yield, molecular weight, and polymer dispersity of poly-IPXTC (PIPXTC) increased with longer polymerization times. After 3 hours of polymerization, the molecular weight reached a maximum

TABLE 8

Homopolymerization of IPXTC with coordinative and anionic catalysts

| Entry | Catalyst. | IPXTC/Cat | Solvent | Temp. (° C.) | Time (h) | Yield (%) | Mn | Mw/Mn | $[\alpha]^{25}_{589}$ |
|---|---|---|---|---|---|---|---|---|---|
| 1 | MAO | 25 | DOX | 70 | 48 | 67 | 5380 | 1.21 | −17.0 |
| 2 | MAO | 25 | DOX | 70 | 96 | 44 | 1010 | 1.20 | −4.2 |
| 3 | MAO | 100 | DOX | 70 | 24 | <2 | — | — | |
| 4 | IBAO | 25 | DOX | 70 | 48 | 61 | 755 | 1.30 | −3.86 |
| 5 | IBAO | 25 | DOX | 70 | 96 | 53 | 1020 | 1.16 | |
| 6 | AlEt$_3$-0.5H$_2$O | 25 | DOX | 70 | 48 | 52 | 1824 | 1.26 | −2.63 |
| 7 | ZnEt$_2$-0.5H$_2$O | 25 | DOX | 70 | 48 | 73 | 2490 | 1.23 | −14.6 |
| 8 | ZnEt$_2$-0.5H$_2$O | 25 | DOk | 70 | 96 | 69 | 1732 | 1.43 | −12.1 |
| 9 | ZnEt$_2$-0.5H$_2$O | 50 | DOX | 70 | 48 | 80 | 2058 | 1.36 | −12.1 |
| 10 | ZnEt$_2$-0.5H$_2$O | 100 | DOX | 70 | 24 | 50 | 3750 | 1.88 | −26.0 |
| 11 | Et$_2$AlOEt | 100 | DOX | 70 | 24 | 14 | — | — | |
| 21 | $^t$BuOK | 100 | DOX | 25 | 0.4 | 10 | 2450 | 1.22 | −19.0 |
| 22 | $^t$BuOK | 100 | DOX | 25 | 1 | 34 | 6770 | 1.52 | −21.2 |
| 23 | $^t$BuOK | 100 | DOX | 25 | 3 | 44 | 9780 | 1.72 | −21.0 |
| 24 | tBuOK | 100 | DOX | 25 | 11 | 56 | 6450 | 1.97 | −21.0 |

TABLE 9

Homopolymerization of IPXTC catalyzed by yttrium isopropoxide$^a$

| Entry | IPXTC/Y | Solvent | Temp. (° C.) | Time (h) | Yield (%) | Mn | Mw/Mn | $[\alpha]^{25}_{589}$ |
|---|---|---|---|---|---|---|---|---|
| 1 | 100 | THF | 25 | 8 | 12 | — | — | |
| 2 | 100 | THF | 25 | 24 | 4 | — | — | |
| 3 | 100 | DOX | 25 | 3 | 10 | 2450 | 1.22 | −19.0 |
| 4 | 100 | DOX | 25 | 8 | 34 | 4600 | 1.25 | −21.1 |
| 5 | 100 | DOX | 25 | 24 | 24 | 4290 | 1.29 | −21.1 |
| 6 | 50 | CH$_2$Cl$_2$ | 70 | 24 | 35 | 2110 | 1.42 | −19.7 |
| 7 | 100 | Toluene | 70 | 24 | 45 | 2570 | 1.88 | −19.7 |
| 8 | 100 | DOX | 70 | 1 | 15 | 4250 | 1.47 | 19.2 |
| 9 | 100 | DOX | 70 | 3 | 58 | 13200 | 1.69 | −19.7 |
| 10 | 100 | DOX | 70 | 6 | 62 | 12800 | 1.71 | 21.4 |
| 11 | 100 | DOX | 70 | 16 | 69 | 11300 | 1.83 | −21.4 |
| 12 | 100 | DOX | 70 | 24 | 75 | 9180 | 1.75 | −21.8 |
| 13 | 100 | DOX | 70 | 48 | 64 | 4260 | 1.76 | −21.4 |
| 14 | 200 | DOX | 70 | 36 | 44 | 8150 | 1.92 | −24.5 |

AlEt$_3$-H$_2$O and ZnEt$_2$-H$_2$O showed very low activity for the polymerization of IPXTC and usually only polymers with very low molecular weight were formed. For example, when MAO was used as the catalyst, 48 hours of polymerization gave only about 60% polymer with a molecular weight of several remained unchanged, rather than being converted into polymer or oligmers. The low activity of this kind of catalyst for the homopolymerization of IPXTC may be due to the fact that bulky IPXTC molecules were difficult to activate by coordinating with the metal ions (M+) of the catalysts, which is needed for the polymerization of cyclic esters or carbonates with coordinative catalysts.

The catalyst $^t$BuOK is a typical anionic catalyst for the polymerization of ϵ-caprolactone. Under the same conditions as described above, the polymerization finished in of 9750, and then declined, but the yields of PIPXTC still increased slowly. At the same time, the polymer dispersity became very broad. This suggests that there were transesterification reactions during the polymerization. Actually, IPXTC oligmers was observed by GPC after 1 hour of polymerization.

It is already established that anionic polymerization of cyclic esters is in equilibrium between linear polymers and oligmers. It was also found that at an elevated temperature, e.g., 70° C., the transesterification reaction became much more of a dominant, and undesired reaction.

Rare earth alcholates were found to be very effective for the ring opening polymerization of ϵ-caprolactone and lactide and cyclic carbonates, but caused much slower transesterification during the polymerization than alkaline metal alcholates. Therefore the effect of yttrium isopropoxide on the polymerization of IPXTC was analyzed. The results are summarized in Table 9.

At room temperature, Y(OiPr)$_3$ catalyzed IPXTC polymerization very slowly in THF. For example, after 8 hours, only 12% of the IPXTC was converted to a polymer with molecular weight of 2540. Longer polymerization time, e.g., 24 hours, did not increase yields and molecular weight but decreased both. In dioxane, Y(OiPr)$_3$ had higher activity towards the polymerization of IPXTC. The yield and molecular weight of the polymer increased steadily early in the polymerization, then reached a maximum, 34% of the yield and a molecular weight of 4600, after 8 hours of polymerization. At room temperature, the molecular weight distribution of the polymer was narrow, about 1.2, but became broader as the polymerization proceeded.

At elevated an temperature, i.e., 70° C., the maximum yield and molecular weight of PIPXTC substantially increased. For example, the yield and molecular weight of PIPXTC were higher than 70% and 1.0×10$^4$, respectively. However, the yield and molecular weight of PIPXTC did not reach their maximum points simultaneously. The molecular weight of PIPXTC reached 1.32×10$^4$ after 1 hour of polymerization with 58% yield, then decreased gradually, i.e., to 1.28×10$^4$ after 3 hours, 1.13×10$^4$ after 16 hours, and to 0.92×10$^4$ after 24 hours of polymerization, while the yield of the polymer increased rapidly early in the polymerization (before 3 hours), then gradually increased up to 75% after 24 hours of polymerization, and then decreased gradually. The molecular weight distribution of PIPXTC was narrow early in the polymerization, and became broader as the polymerization proceeded. These results suggest that the decrease in yield and molecular weight was ascribed to the backbiting degradation, i.e., transesterification reactions. These reactions proceeded predominately over the propagaton reaction later in the polymerization.

Example 8

Copolymerization of TMC and IPXTC

The effects of different catalysts, comonomer feed ratio ($f_{TMC}/f_{IPXTC}$), and reaction temperature on the IPXTC-[L]-TMC copolymer yield, molecular weight, and composition ($F_{TMC}/F_{IPXTC}$) are shown in Table 10. Polymerizations illustrated in Table 10 were performed at 90° C., with a (TMC+ IPXTC) to catalyst molar ratio of 200. Polymerization was carried out for 22 hours and the $f_{TMC}/f_{IPXTC}$ ratio was 68/32 (molar).

Figure 2:
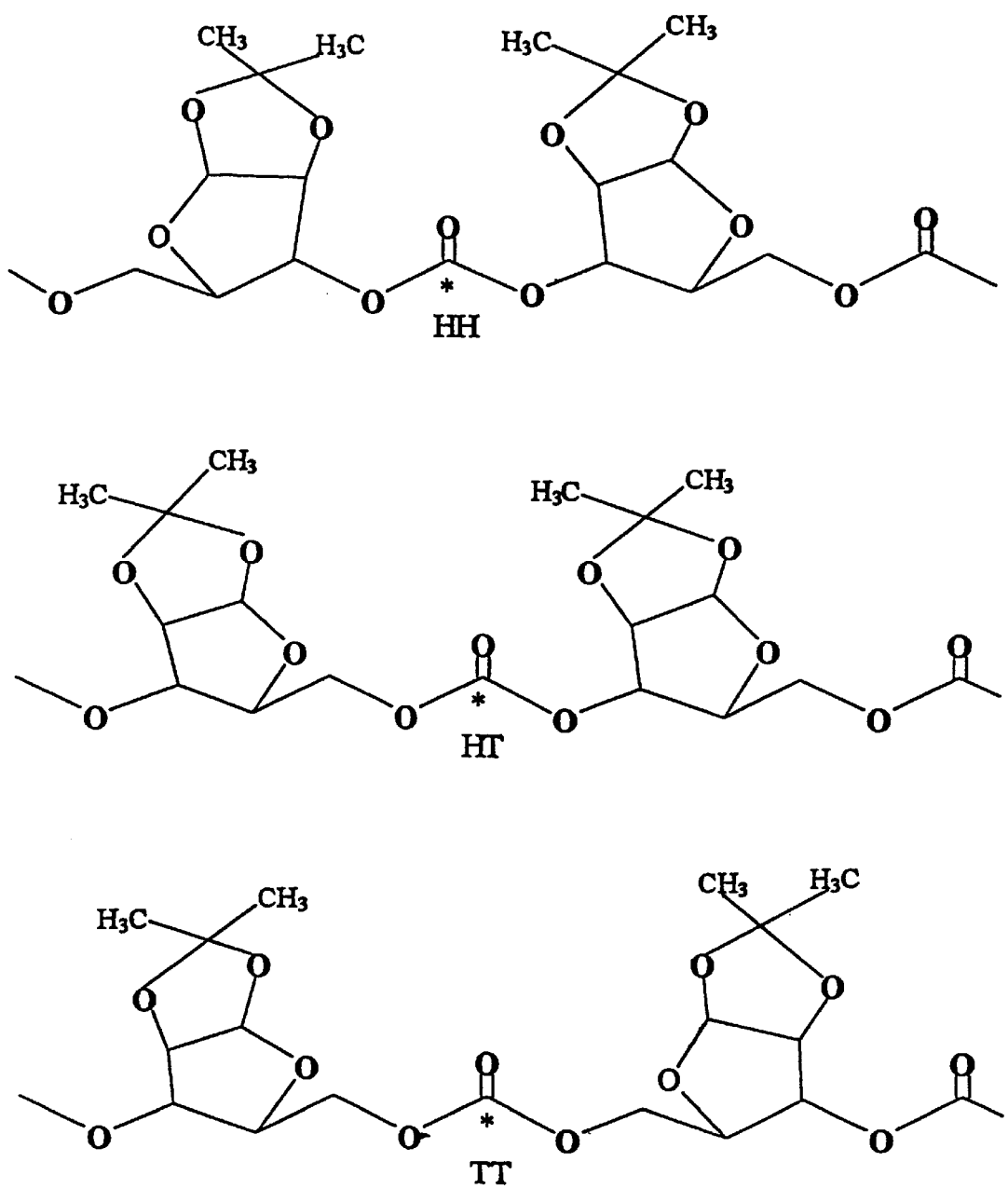
FIG. 2 is a depiction of IPXTC monomers linked to each other in a head to head, head to tail and tail to tail configurations.

The average IPXTC and TMC repeat unit lengths can be calculated by equations 1 and 2, respectively, where I is the peak $^{13}$C-NMR intensity for the particular diad (consecutive sequence of two comonomers) given as a subscript. The diad IP—IP refers to IPXTC—IPXTC diad sequences that are linked head to head, head to tail, or tail to tail. See FIG. 2. The diad IP-TMC refers to the IPXTC-TMC diad sequence. The diad TMC—TMC refers to the TMC—TMC diad sequence. The results of these analyses are given as part of Tables 8 and 12.

$$L_{IPXTC} = [I_{IP-IP}(I_{154.62ppm} + I_{153.96ppm} + I_{153.43ppm}) + I_{IP-TMC}(I_{154.16ppm})] / I_{IP-TMC}(I_{154.16ppm}) \quad \text{Equation 1}$$

$$L_{TMC} = [I_{TMC-TMC}(I_{155.30ppm}) + I_{TMC-IP}(I_{154.94ppm})] / I_{TMC-IP}(I_{154.94ppm}) \quad \text{Equation 2}$$

TABLE 10

TMC-IPXTC copolymerization with various catalyst

| entry | catalyst | yield % | $M_n$ | $M_w/M_n$ | $F_{IPXTC}$ | $L_{TMC}/L_{IPXTC}$ |
|---|---|---|---|---|---|---|
| 1 | AlET$_3$-H$_2$O(1/0.5) | 51 | 11,400 | 1.5 | 77/23 | — |
| 2 | Al$^i$Bu$_3$-H$_2$O(1/0.5) | 52 | 10,300 | 1.5 | 78/22 | — |
| 3 | ZnEt$_2$-H$_2$O(1/0.5) | 95 | 14,700 | 2.3 | 71/29 | 2.82/1.11 |
| 4 | MAO | 92 | 21,700 | 2.1 | 71/29 | 2.28/1.04 |
| 5 | IBAO | 88 | 18,500 | 2.1 | 68/32 | 2.32/1.06 |
| 6 | Sn(Oct)$_2$ | 6 | 3,530 | 1.1 | n.d. | — |

The number average ($M_n$) and weight average ($M_w$) molecular weights were determined by standard, refractive index-detection gas phase chromatography in chloroform at room temperature, with polystyrene serving as the internal standard. The copolymer composition is expressed in mol ratio, and was determined by $^1$H-NMR. Yield values were determined based on the amount of methanol insoluble copolymer at the end of the reaction. The copolymerization was carried out for 6 hours, in bulk, with a comonomer/catalyst ratio of 200:1.

It has been demonstrated that Al-based organometallics and Sn(Oct)$_2$ are effective catalysts for the ring-opening polymerization of cyclic carbonates and lactides. Therefore, alkyl aluminum-water, ZnEt$_2$-H$_2$O, MAO, and IBMO systems were tested as the catalysts for the ring-opening copolymerization of TMC and IPXTC The molar feed ratio of TMC to IPXTC was fixed at 68/32, the polymerization temperature and reaction time were 90° C. and 22 hours, respectively. The results listed in Table 10 show that Sn(Oct)$_2$ showed very low activity for the copolymerization. The alkyl aluminium-H$_2$O (1/0.5) systems showed only modest activity. The most promising results were obtained using the ZnEt$_2$-H$_2$O, MAO, and IBAO catalysts. For example, using the MAO catalyst, the %-yield was 92 after 22 hours and the copolymer $M_n$ was 21700 g/mol.

Tables 11 and 12 show the results of TMC/IPXTC copolymerizations where the monomer feed was varied and the catalysts were ZnEt$_2$-0.5H$_2$O and MAO, for Tables 11 and 12 respectively. Conditions as in Table 10.

TABLE 11

Copolymerization of TMC with IPXTC catalyzed by ZnEt$_2$-H$_2$O(1/0.5) at different feed ratios

| entry | $f_{TMC}/f_{IPXTC}$ | yield % | Mn | Mw/Mn | $F_{TMC}/F_{IPXTC}$ |
|---|---|---|---|---|---|
| 1 | 0/100 | 1.4 | n.d. | 1.5 | 0/100 |
| 2 | 10/90 | 45 | 5,230 | 1.8 | 17/83 |
| 3 | 30/70 | 69 | 6,470 | 2.3 | 38/62 |
| 4 | 50/50 | 95 | 15,700 | 2.2 | 54/46 |
| 5 | 68/32 | 95 | 14,700 | 2.3 | 71/29 |
| 6 | 90/10 | 95 | 16,500 | 2.2 | 92/8 |
| 7 | 100/0 | 91 | 16,900 | 2.5 | 100/0 |

TABLE 12

TMC-IPXTC copolymerization by MAO at various monomer feed ratio:

| entry | $f_{TMC}/f_{IPXTC}$ | Polym. Time (h) | yield % | Mn | Mw/Mn | $F_{TMC}/F_{IPXTC}$ |
|---|---|---|---|---|---|---|
| 1 | 10/90 | 22 | 39 | 5000 | 1.5 | 19/81 |
| 2 | 30/70 | 22 | 64 | 4160 | 2.8 | 40/60 |
| 3 | 50/50 | 22 | 75 | 20660 | 2.7 | 57/43 |
| 4 | 70/30 | 2 | 95 | 20900 | 2.5 | 71/29 |
| 5 | 90/10 | 2 | 98 | 35000 | 2.1 | 93/7 |
| 6 | 100/0 | 2 | 98 | 52000 | 2.2 | 100/0 |

When the IPXTC content for both of these catalysts was increased from 50 to 70 mol %, the resulting copolymer $M_n$ and/or %-yield values decreased substantially. Inspection of entry 1 of Tables 11 and 12 shows that the homopolymerization of IPXTC under the present reaction conditions was sluggish. A similar detrimental effect of bulky substituents was found for the polymerizations of the cyclic carbonates, 2-methyl-2-phenyltrimethylene carbonate, 2,2-diphenyltrimethylene carbonate and 5,5-(bicyclo[2,21]hept-2-en-5,5-diylidene)-1,3-dioxan-2-one. These results provided evidence that the bulky substituents of IPXTC make it difficult to form IPXTC—IPXTC diads along the copolymer chains. However, the results in Tables 11 and 12 also show good agreement between the monomer feed and polymer compositions. Considering the above, these results suggest that the formation of TMC-IPXTC and/or IPXTC-TMC diads is favorable.

Table 12 also shows that when the polymerization time was reduced to $\leq 2$ hours, high copolymer molecular weights and conversions were achieved for MAO catalyzed TMC/IPXTC copolymerizations with $\geq 70$ mol % TMC in the monomer feed. This result inspired further studies on the influence of reaction time that are described below.

The effect of reaction time was evaluated by fixing the TMC/IPXTC feed ratio at 68/32, the reaction temperature at 90° C., and the monomer/catalyst molar ratio at 200. For the MAO catalyzed polymerizations (Table 13), the $M_n$ and conversion increased regularly with increase in the reaction time from 0.5 to 2.0 hours. Polymerizations were carried out at 90° C. with a (TMC+IPXTC)/Al molar ratio of 200. The $f_{TMC}/f_{IPXTC}$ molar ratio was 68/32.

Extending the reaction time to 2 hours was sufficient to reach a 96% yield. As above, early stages of the polymerization gave copolymers that had a higher content of IPXTC than was given in the monomer feed. Extending the polymerization time from 4 to 22 hours when using the $ZnEt_2$-$0.5H_2O$ catalyst lead to chain scission reactions (see entries 4 and 5, Table 14).

Example 9
Alternating Character of the TMC-IPXTC Copolymers

The reactivity ratios of TMC and IPXTC determined by the method of Fineman-Ross (Odian, G. *Principles of Polymerization* 3rd Ed., Wiley-Interscience, John Wiley & Sons, Inc.: New York, 1991, p. 469) were 0.20 and 0.31, respectively, when using $ZnEt_2$-$0.5H_2O$ as the catalyst, at 90° C. and a monomer/catalyst ratio of 200. This was very different from the results of IPXTC/[L]-LA copolymerizations in which a wide range of Al-, Zn-, and Sn-based catalysts had a much lower reactivity with IPXTC than [L]-LA.

The average IPXTC ($L_{IPXTC}$) and TMC ($L_{TMC}$) chain segment lengths were determined by $^{13}$C-NMR as described above. This work was conducted for copolymers produced by the Al- and Zn-based catalysts that were used in this study (see Tables 10 and 14). In all of cases, the monomer feed ratio (TMC:IPXTC) was fixed at 68/32, and the polymerization temperature was held at 90° C. Observation of Tables 10 and 14 shows that $L_{IPXTC}$ for the copolymers prepared using MAO, IBAO, and $ZnEt_2$-$0.5H_2O$ as the catalysts were close in value to 1.0. This is consistent with the discussion above that the kinetics of formation of IPXTC—IPXTC diads is relatively slow. In addition, this agrees with the

TABLE 13

TMC-IPXTC copolymerization catalyzed by MAO at different time.

| Entry | Time (h) | TMC Conv. (%) | IPXTC Conv. (%) | Overall Conv. (%) | Mn | Mw/Mn | $F_{TMC}/F_{IPXTC}$ |
|---|---|---|---|---|---|---|---|
| 1 | 0.5 | 38.7 | 67.3 | 53 | 8900 | 1.9 | 55/45 |
| 2 | 1.0 | 65.8 | 82.2 | 74 | 15000 | 2.3 | 63/37 |
| 3 | 1.5 | 88 | 85.2 | 86 | 18000 | 2.1 | 69/31 |
| 4 | 2.0 | 96 | 96 | 96 | 22000 | 2.1 | 68/32 |
| 5 | 22 | — | — | 92 | 21700 | 2.1 | 71/29 |

A further increase in the reaction time did not substantially change the copolymer molecular weight and composition. A similar study using $ZnEt_2$-$0.5H_2O$ as the catalyst was also conducted. A large increase in the %-yield and Mn was observed from 0.5 to 1 hour (Table 14). $L_{TMC}$ and $L_{IPXTC}$ are the average IPXTC and TMC repeat unit lengths as defined above. Other polymerization conditions were as described in Table 13.

values of reactivity ratios reported above. Hence, a propagating chain end containing an IPXTC unit at the terminus will tend to add a TMC repeat unit. Also, the reactivity ratio values using $ZnEt_2$-$0.5H_2O$ as the catalyst show, at least for the Zn system, that a propagating chain end containing a TMC unit at the terminus will tend to add an IPXTC unit. In other words, this work has lead to methods for the prepa-

TABLE 14

Effect of the reaction time on the TMC-IPXTC copolymerization using $Zn_2Et_2$-$0.5H_2O$ catalyst

| entry | time (h) | TMC Conv. (%) | IPXTC Conv. (%) | Overall yield (%) | $M_n$ | $M_w/Mn_n$ | $F_{TMC}/F_{IPXTC}$ | $L_{TMC}/L_{IPXTC}$ |
|---|---|---|---|---|---|---|---|---|
| 1 | 0.5 | 28 | 50 | 39 | 10,900 | 1.8 | 54/46 | 1.38/1.44 |
| 2 | 1 | 76 | 90 | 83 | 17,300 | 2.0 | 64/36 | 2.35/1.35 |
| 3 | 2 | 96 | 96 | 96 | 18,200 | 2.0 | 68/32 | 2.41/1.17 |
| 4 | 4 | 98 | 98 | 98 | 19,300 | 2.0 | 68/32 | 2.28/1.04 |
| 5 | 22 | — | — | 95 | 14,700 | 2.2 | 71/29 | 2.72/1.05 | ration of TMC/IPXTC copolymers that have a tendency towards an alternating copolymer microstructure.

Example 10
Preparation of Hydroxyl-Functionalized Polycarbonate by Deprotection

An important component of this work was to transform the ketal-protected functionalities along the TMC-IPXTC copolymer chain to vicinol-diol groups. Preliminary experiments for this purpose showed that $CF_3COOH/H_2O$ in $CH_2Cl_2$ was the preferred deprotection system. Studies using $BCl_3$ for deprotection were not successful due to extensive chain scission that occurred concomitantly with ketal hydrolysis. Other investigations using $FeCl_3$ and $PdCl_2$ showed that these catalysts were useful for deprotection, but were difficult to remove from the deprotected product.

In the case of 37 mol % IPXTC, the extent of deprotection was 47 mol % as measured by the $^1$H-NMR signal of the ketal group. In other words, 47% of the IPXTC repeat units were converted to the corresponding vicinol diol. The effect of different times of reaction with $CF_3COOH/H_2O$ in $CH_2Cl_2$ at room temperature on the extent of poly(TMC-CO-29% IPXTC) copolymer deprotection is shown in Table 15. $T_p$ is the physical aging transition temperature. $\Delta H_p$ is the physical aging enthalpy.

1736; $-12°$) and 128° C., respectively. Comparison of the experimental and calculated (Fox equation) $T_g$ values showed that they were in excellent agreement over the full range of copolymers studied (Table 16).

TABLE 16

The thermal properties of TMC-IPXTC copolymers with different compositions

| entry | $F_{TMC}/F_{IPXTC}$ | Tp (° C.)$^a$ | $\Delta$Hp (J/g)$^b$ | Tg (° C.)$_{Calcu}{}^c$ | Tg (° C.) |
|---|---|---|---|---|---|
| 1 | 0/100 | — | — | — | 128 |
| 2 | 17/83 | 115 | 6.5 | 108 | 109 |
| 3 | 38/62 | 88 | 10.0 | 83 | 82 |
| 4 | 54/46 | 62 | 3.4 | 60 | 62 |
| 5 | 71/29 | 40 | 6.29 | 35 | 37 |
| 6 | 77/23 | 32 | 0.91 | 25 | 28 |
| 7 | 92/8 | — | — | 0.96 | 3 |
| 8 | 100/0 | — | — | — | −13 |

This is consistent with a copolymer microstructure that tends towards alternating. It is also noteworthy that all of the thermograms for entries 1 to 7 of Table 16 showed only one $T_g$.

The first heating scan of the IPXTC homopolymer as well as poly(TMC-co-IPXTC) with IPXTC contents $\geq$23% showed prominent endotherm peaks that were not resolved

TABLE 15

The Deprotection of poly(TMC-co-29% IPXTC) copolymer

| Entry | Deprotection Time (min) | Deprotection Degree (%) | % of OH group (mole) | Mn | Mn/Mn° | Mw/Mn | Tp (° C.)$^a$ | $\Delta$Hp (J/g)$^b$ | Tg (° C.) |
|---|---|---|---|---|---|---|---|---|---|
| 1 | 0 | 0 | 0 | 21700 | 1.0 | 2.1 | 46 | 3.5 | 38 |
| 2 | 5 | 47.6 | 27.6 | 20900 | 0.96 | 1.8 | 41 | 3.4 | 34 |
| 3 | 10 | 85.4 | 49.5 | 18600 | 0.86 | 1.67 | 38 | 3.40 | 31 |
| 4 | 20 | 95.2 | 55.2 | 16600 | 0.76 | 1.55 | 35 | 2.35 | 28 |

High levels of deprotection (95%) were reached by extending the reaction to 20 minutes. The fractional molecular weight change resulting from the time of the deprotection reaction was determined by using values of $M_n°/M_n$ where $M_n°$ is the molecular weight of the starting copolymer. Values of $M_n/M_n°$ for reaction times of 5, 10, arid 20 minutes are 0.96, 0.86 and 0.76, respectively (see Table 15). However, it should be noted that the molecular weights were determined relative to polystyrene so that changes in the hydrodynamic volume were not taken into account. As the extent of deprotection increased, copolymer solubility in chloroform and dichloroethane decreased. Instead, poly (TMC-co-29% IPXTC) that was 95% deprotected was now soluble in N,N-dimethyl formamide and insoluble in chloroform.

Example 11
Thermal Properties

Differential scanning calorimetry (DSC) was used to study the thermal properties of TMC-IPXTC copolymers both prior to and after deprotection. Poly(TMC-co-IPXTC) products that contain 62, 29, and 8 mol % IPXTC repeat units (Table 16: entries 3, 5, and 7, respectively) resulted from $ZnEt_2$-$H_2O$ (1/0.5) catalyzed polymerizations (90° C., 22 hours) that were carried out to high conversion (>90%). The extremes of the $T_g$ range for TMC-IPXTC copolymers are defined by the values of the respective homopolymers. Study of the second heating scans showed that TMC and IPXTC homopolymers have $T_g$ values of −13 (Zhu, K. J.; Hendren, K.; and Pitt, C. G. *Macromolecules* 1991, 24, from $T_g$ transitions. The IPXTC homopolymer is semicrystalline. The WAXS patterns on the copolymer samples in Table 16 showed only an amorphous halo with no crystalline reflections. In addition, work by Zhu et al. (Zhu, K. J.; Hendren, K.; and Pitt, C. G. *Macromolecules* 1991, 24, 1736) showed that high molecular weight PTMC was difficult to crystallize. Interestingly, the average IPXTC segment lengths of poly(TMC-co-IPXTC) with 83 and 62 mol % IPXTC were only 4.86 and 2.53, respectively. For copolymers with $\leq$32 mol % IPXTC units, the average IPXTC segment length is near 1.0. Hence, it is understandable that the IPXTC components of the copolymers did not crystallize. It was concluded that the endothermic peaks near $T_g$ transitions in the first heating scans correspond to physical aging rather than melting (FIG. 4, Table 16). The physical aging transition temperature decreased with decreasing mol % IPXTC in the copolymers (Table 16). The enthalpy of this transition ($\Delta H_p$) varied irregularly from about 6 to 10 J/g for copolymer compositions ranging from 29 to 83 mol % IPXTC. At low IPXTC copolymer content ($\leq$8 mol %, Table 16), the physical aging transition was not observed.

The DSC thermograms of the deprotected copolymers were very similar to those of the corresponding protected copolymers. In the first DSC scans, the deprotected copolymers showed prominent physical aging transitions (see Table 15). It is interesting to consider whether the $T_g$ will increase or decrease with higher extents of IPXTC deprotection. Taking steric bulk as an independent parameter, the removal of the ketal group would cause the $T_g$ to decrease. However, the transition of the ketal to a vicinal diol may introduce effects of hydrogen bonding that would tend to increase the $T_g$. Observation of Table 15 shows that by increasing the extent of deprotection from 0 to 95.2% for poly(TMC-co-29% IPXTC), the $T_g$ decreased from 38 to 29° C.

Example 12
Filament Preparation

Filaments of any of the copolymers presented herein can be prepared as follows. First, to determine the conditions for fiber production, samples of the copolymer, dried under a flow of nitrogen (dew point <−60° C.), are heated in the chamber of a capillary rheometer to a temperature above the melting point of the polymer. Monofilament samples are extruded at various temperatures and the viscosities are determined at these temperatures.

Second, dried polymer is then fed from a hopper designed to prevent contact of the polymer with atmospheric moisture, and extruded through a single-screw extruder fitted with a gear pump and multifilament die. The temperature is chosen so that the viscosity of the melt is between 700 and 1200 sec⁻. The filament is taken up over a lube godet and fed to a draw-frame. Speeds are adjusted to provide filaments with 10–50% elongation at break.

Example 13
Molded Products

Molded products of any of the polymers presented herein can be prepared by drying the resin under a flow of nitrogen at a temperature slightly above room temperature in a resin injection pot fitted to a molding machine. The polymer is molded at a temperature above the flow point into a desired shape. The molded product can then optionally be annealed using standard techniques to develop a desired degree of crystallinity. The molded product is then cooled and removed from the mold.

A wide variety of medical devices can be manufactured from the polymers of this invention. These include, but are not limited to, sutures, staples, clips and other fasteners, wound dressings, drug delivery devices, pins, screws and other implants.

Example 14
Solid Insulin Compositions

Solid drug compositions and devices suited for insulin therapy can be prepared from the new copolymers. The devices are small enough to be implanted subcutaneously or interperitoneally and are designed to dispense precise amounts of a drug over prolonged periods of time. For example, the solid drug filaments can be prepared so that they are stable and provide a high dosage per unit volume.

To produce a sustained-release insulin dispensing composition, human recombinant insulin (HRI) is mixed with a bioresorbable copolymer of the invention to provide a solid filament containing insulin. The above protocol is performed by mixing 0.2 g of bioresorbable polymer and approximately 0.02 g HRI. The mixture is extruded through a 2.3 mm syringe (0.3 mm internal diameter needle) with a syringe pump. The filaments are extruded and dried under vacuum for 24 hours, and are examined for homogeneity, stability, and solidity.

The filaments are then tested in terms of pharmaceutical activity by implanting given lengths of filaments into beagle dogs subcutaneously. The hypoglycemic effect of the filaments is measured and compared to the same dosage administered as a liquid insulin solution. Similarly, bovine pancreas insulin (BPI) is mixed with the bioresorbable copolymer of the invention to form a solid drug composition containing bovine pancreas insulin.

Example 15
Solid SOMATULINE™ Compositions

Filaments are also made with a somatostatin analog, SOMATULINE™ (BIM 23014C, Biomeasure, Milford Mass.) and a bioresorbable polymer of the invention to produce a solid composition containing SOMATULINE™.

The above protocol is performed by mixing approximately 0.4 g of bioresorbable polymer with approximately 0.06 g BIM 23014. The mixture is extruded through a 2.3 mm syringe (0.3 mm internal diameter needle), collected, and dried under vacuum for 24 hours. The dried filament contains BIM 23014. The filaments are tested for pharmacokinetics and compared to liquid infusions of the same dosage of SOMATULINE™ in dogs.

Other Embodiments

It is to be understood that while the invention has been described in conjunction with the detailed description thereof, the foregoing description is intended to illustrate and not limit the scope of the invention, which is defined by the scope of the appended claims. Other aspects, advantage and modifications are within the scope of the following claims.

What is claimed is:

1. A bioresorbable copolymer composition comprising products of a reaction between:
   a) a first comonomer comprising lactones, lactides, lactams, thiolactones, or nonfunctionalized cyclic carbonates; and
   b) a second, functionalized, cyclic carbonate comonomer, wherein said second comonomer is functionalized by a substituent group comprising alkenes, alkynes, protected hydroxyl groups or protected carboxyl groups.

2. A bioresorbable copolymer composition of claim 1, wherein the first comonomer is a lactone.

3. A bioresorbable copolymer composition of claim 1, wherein the first comonomer is lactide.

4. A bioresorbable copolymer composition of claim 1, wherein the first comonomer is [L]-lactide.

5. A bioresorbable copolymer composition of claim 1, in which the second, functionalized, cyclic carbonate comonomer has the formula

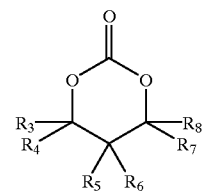

wherein $R_3$, $R_4$, $R_5$, $R_6$, $R_7$ and $R_8$ are substituent groups comprising hydrogen atoms, alkenes, alkynes, protected hydroxyl groups or protected carboxyl groups; with the proviso that not all R groups are hydrogen.

6. A bioresorbable copolymer composition of claim 5, wherein any of $R_3$, $R_4$, $R_5$, $R_6$, $R_7$, and $R_8$ form cyclic linkages with each other.

7. A bioresorbable copolymer composition of claim 5, wherein the second, functionalized, cyclic carbonate comonomer comprises an alkene.

8. A bioresorbable copolymer composition of claim 5, wherein the second, functionalized, cyclic carbonate comonomer comprises a ketal.

9. A bioresorbable copolymer composition of claim 6, in which the functionalized cyclic carbonate comonomer is selected from the group consisting of 2,4-dioxaspiro[5.5]

undec-8-ene-3-one (HTC), 1,2-O-isopropylidene-D-xylofuranose-3,5-cyclic carbonate (IPXTC), and 9,9-dimethyl-2,4,8,10-tetraoxaspiro[5.5]undecan-3-one (DTOUD).

10. A bioresorbable copolymer composition of the formula

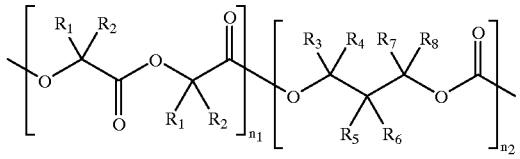

wherein $n_1$ and $n_2$ are 1 to 20,000; $R_1$ and $R_2$ are hydrogen, short chain or medium chain alkyl; and $R_3$, $R_4$, $R_5$, $R_6$, $R_7$ and $R_8$ are substituent groups comprising hydrogen atoms, alkenes, amines, carboxyl groups, thiols, epoxides, hydroxyl groups, esters, ethers, amides, thioethers, protected thiol groups, protected carboxyl groups, or protected hydroxyl groups; with the proviso that not all R groups are hydrogen.

11. A bioresorbable copolymer composition of the formula

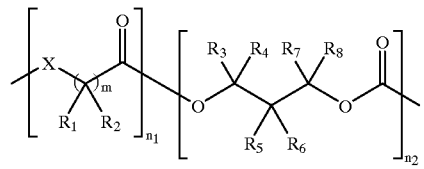

wherein m is 1 to 5; X is NH or S; $n_1$ and $n_2$ are 1 to 20,000; $R_1$ and $R_2$ are hydrogen, short chain or medium chain alkyl; and $R_3$, $R_4$, $R_5$, $R_6$, $R_7$ and $R_8$ are substituent groups comprising hydrogen atoms, alkenes, amines, carboxyl groups, thiols, epoxides, hydroxyl groups, esters, ethers, amides, thioethers, protected thiol groups, protected carboxyl groups, or protected hydroxyl groups; with the proviso that not all R groups are hydrogen.

12. A bioresorbable copolymer composition of the formula

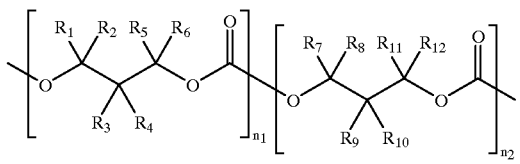

wherein $n_1$ and $n_2$ are 1 to 20,000; $R_1$, $R_2$, $R_3$, $R_4$, $R_5$, and $R_6$ are substituent groups comprising hydrogen atoms, alkanes, and ethers; and $R_7$, $R_8$, $R_9$, $R_{10}$, $R_{11}$ and $R_{12}$ are substituent groups comprising hydrogen atoms, alkenes, amines, carboxyl groups, thiols, epoxides, hydroxyl groups, esters, ethers, amides, thioethers, protected thiol groups, protected carboxyl groups, or protected hydroxyl groups; with the proviso that not all $R_7$, $R_8$, $R_9$, $R_{10}$, $R_{11}$ and $R_{12}$ are hydrogen.

13. A method of preparing a functionalized bioresorbable copolymer composition, the method comprising the steps of:
   (a) obtaining a first comonomer comprising lactones, lactams, thiolactones, or nonfunctionalized cyclic carbonates;
   (b) obtaining a second, functionalized, cyclic carbonate comonomer, wherein said second comonomer is functionalized by a substituent group comprising alkenes, alkynes, protected hydroxyl groups, or protected carboxyl groups; and,
   (c) carrying out a copolymerization reaction between said first comonomer and said second, functionalized, cyclic carbonate comonomer under conditions which allow the formation of a functionalized bioresorbable copolymer composition.

14. A method of claim 13, wherein the copolymerization is catalysed with a catalyst is selected from the group consisting of $Sn(Oct)_2$, $ZnEt_2\text{-}H_2O$, $AlEt_3$, $Al(isobutyl)_3$, $Al(O\text{-secbutyl})_3$, $Al(O\text{-isopropyl})_3$, $Sn(C_6H_5)_4$, $La(OR)_3$, and $Y(OR)_3$, wherein R is ethyl, isobutyl, secbutyl, or isopropoxyl.

15. A method of claim 13, further comprising the step of epoxidizing alkene groups of the functionalized bioresorbable copolymer subsequent to carrying out the copolymerization reaction, thereby creating epoxide groups.

16. A method of claim 15, further comprising the step of converting the epoxide groups of the functionalized bioresorbable copolymer to hydroxyl groups subsequent to epoxidizing the alkene groups.

17. A method of claim 13, further comprising the step of removing the hydroxyl protecting groups of the functionalized bioresorbable polymer subsequent to carrying out the catalysed copolymerization reaction, thereby introducing hydroxyl groups.

18. A method of claim 16, further comprising the step of further functionalizing the hydroxyl groups, wherein said hydroxyl groups are functionalized by a substituent group comprising esters, ethers, amines, and carboxylic acids.

19. A method of claim 17, further comprising the step of further functionalizing the hydroxyl groups, wherein said hydroxyl groups are functionalized by a substituent group comprising esters, ethers, amines, and carboxylic acids.

20. A pharmaceutically active bioresorbable copolymer composition comprising:
   (a) a bioresorbable copolymer composition of any one of claims 10–12; and
   (b) a pharmaceutically active substance linked to the copolymer.

21. A pharmaceutically active bioresorbable copolymer composition of claim 20, wherein the pharmaceutically active substance is selected from the group consisting of proteins, glycoproteins, anticancer drugs, and antihypertensive drugs.

22. A method of making a pharmaceutically active bioresorbable copolymer composition, the method comprising the steps of:
   (a) producing a bioresorbable copolymer composition by a synthesis method, the synthesis method comprising the steps of:
      (i) obtaining a first comonomer comprising lactones, lactams, thiolactones, or nonfunctionalized cyclic carbonates;
      (ii) obtaining a second, functionalized, cyclic carbonate comonomer, wherein said second comonomer is functionalized by a substituent group comprising alkenes, alkynes, protected carboxyl groups, or protected hydroxyl groups; and,
      (iii) carrying out a copolymerization reaction between said first comonomer and said second, functionalized, cyclic carbonate comonomer under conditions which allow the formation of a functionalized bioresorbable copolymer composition; and
   (b) contacting said bioresorbable copolymer composition with a pharmaceutically active substance under conditions which allow bonding between the copolymer and the pharmaceutically active substance.

23. The method of claim 22, wherein the pharmaceutically active substance comprises a protein, glycoprotein, anticancer drug, or antihypertensive drug.

24. The method of claim 13, further comprising the step of carrying out thermal processing on the bioresorbable copolymer composition.

25. The method of claim 22, further comprising the step of carrying out thermal processing on the pharmaceutically active bioresorbable copolymer composition.

26. The method of claim 25, wherein the thermal processing is chosen from the group consisting of foam formation, film formation, molded product formation, laminate formation, filament formation, adhesive formation, and coating formation.

27. The method of claim 26, wherein the thermal processing is chosen from the group consisting of foam formation, film formation, molded product formation, laminate formation, filament formation, adhesive formation, and coating formation.

28. The method of claim 13, further comprising the step of crosslinking the bioresorbable copolymer with a crosslinking substance.

29. The method of claim 13, further comprising the step of reacting the functionalized, bioresorbable copolymer composition with a monomer comprising lactones, lactams, thiolactones, unfunctionalized cyclic carbonates, functionalized cyclic carbonates, and N-carboxy anhydrides, thereby forming a graft copolymer.

30. The method of claim 13, further comprising the step of reacting the functionalized, bioresorbable copolymer composition with a second bioresorbable copolymer, thereby forming a graft copolymer.

31. A article of manufacture comprising the pharmaceutically active bioresorbable copolymer composition of claim 20.

32. A functionalized cyclic carbonate comonomer 1,2-O-isopropylidene-D-xylofuranose-3,5-cyclic carbonate (IPXTC).

33. A functionalized cyclic carbonate comonomer 2,4-dioxaspiro[5.5]undec-8-ene-3-one (HTC).

34. A functionalized cyclic carbonate comonomer 9,9-dimethyl-2,4,8,10-tetraoxaspiro[5.5]undecan-3-one (DTOUD).

35. A homopolymer comprising a functionalized cyclic carbonate comonomer of claim 32.

36. A bioresorbable copolymer composition comprising IPXTC of claim 32 and TMC.

37. The bioresorbable copolymer composition of claim 36, wherein IPXTC is present in an amount of from 10–70 mole percent.

38. The composition of claim 37, wherein IPXTC is present in an amount of from 20–50 mole percent.

39. The bioresorbable copolymer composition of claim 1, wherein said protected hydroxyl groups are protected by hydroxyl protecting groups comprising ketals, acetals or benzyl ethers; and wherein said protected carboxyl groups are protected by carboxyl protecting groups comprising benzyl esters.

* * * * *